(12) United States Patent
Colachis et al.

(10) Patent No.: US 11,037,670 B2
(45) Date of Patent: Jun. 15, 2021

(54) ACTIVITY ASSISTANCE SYSTEM

(71) Applicant: Battelle Memorial Institute, Columbus, OH (US)

(72) Inventors: Samuel Colachis, Columbus, OH (US); Gaurav Sharma, Lewis Center, OH (US); Collin Dunlap, Columbus, OH (US)

(73) Assignee: BATTELLE MEMORIAL INSTITUTE, Columbus, OH (US)

(*) Notice: Subject to any disclaimer, the term of this patent is extended or adjusted under 35 U.S.C. 154(b) by 0 days.

(21) Appl. No.: 17/023,577

(22) Filed: Sep. 17, 2020

(65) Prior Publication Data
US 2021/0082564 A1    Mar. 18, 2021

Related U.S. Application Data

(60) Provisional application No. 62/901,374, filed on Sep. 17, 2019.

(51) Int. Cl.
*G16H 20/70* (2018.01)
*A61B 5/00* (2006.01)
(Continued)

(52) U.S. Cl.
CPC ............. *G16H 20/70* (2018.01); *A61B 5/162* (2013.01); *A61B 5/4064* (2013.01);
(Continued)

(58) Field of Classification Search
CPC ....... G06T 2210/12; G06T 2207/20182; G06T 2207/10016; G06T 7/11; G06T 7/74;
(Continued)

(56) References Cited

U.S. PATENT DOCUMENTS 10,776,423 B2*  9/2020  Kontschieder ......... G06N 20/20
2009/0098519 A1*  4/2009  Byerly .................. G09B 23/28
434/247

(Continued)

OTHER PUBLICATIONS

Burgess et al., "The case for the development and use of "ecologically valid" measures of executive function in experimental and clinical neuropsychology", *Journal of the International Neuropsychological Society*, 2006, vol. 12, pp. 194-209, Cambridge University Press.

(Continued)

*Primary Examiner* — Mia M Thomas
(74) *Attorney, Agent, or Firm* — Fay Sharpe LLP

(57) ABSTRACT

An activity assistance system includes a video camera arranged to acquire video of a person performing an activity, an output device configured to output human-perceptible prompts, and an electronic processor programmed to execute an activity script. The script comprises a sequence of steps choreographing the activity. The execution of each step includes presenting a prompt via the output device and detecting an event or sequence of events subsequent to the presenting of the prompt. Each event is detected by performing object detection on the video to detect one or more objects depicted in the video and applying one or more object-oriented image analysis functions to detect a spatial or temporal arrangement of one or more of the detected objects. Each event detection triggers an action comprising at least one of presenting a prompt via the output device and and/or going to another step of the activity script.

26 Claims, 32 Drawing Sheets

(51) Int. Cl.
*A61B 5/16* (2006.01)
*G06T 7/11* (2017.01)
*G06T 7/73* (2017.01)
*G06K 9/00* (2006.01)

(52) U.S. Cl.
CPC ........ *A61B 5/4076* (2013.01); *G06K 9/00671* (2013.01); *G06T 7/11* (2017.01); *G06T 7/74* (2017.01); *G06T 2207/10016* (2013.01); *G06T 2207/20182* (2013.01); *G06T 2210/12* (2013.01)

(58) Field of Classification Search
CPC .............. G06K 9/00671; A61B 5/4076; A61B 5/4064; A61B 5/162; G16H 20/70
See application file for complete search history.

(56) References Cited

U.S. PATENT DOCUMENTS

| | | | | |
|---|---|---|---|---|
| 2010/0245582 | A1* | 9/2010 | Harel | G08B 13/19695 348/159 |
| 2013/0060166 | A1* | 3/2013 | Friedman | A61B 5/1125 600/595 |
| 2013/0083063 | A1* | 4/2013 | Geisner | G06F 3/013 345/633 |
| 2013/0147899 | A1* | 6/2013 | Labhard | G16H 40/67 348/14.03 |
| 2014/0245141 | A1* | 8/2014 | Yeh | G06F 3/0481 715/708 |
| 2014/0266753 | A1* | 9/2014 | Steffen | G08B 23/00 340/669 |
| 2015/0181038 | A1* | 6/2015 | Fox | H04M 3/5175 379/265.06 |
| 2016/0143571 | A1* | 5/2016 | Suddamalla | A61B 5/165 600/595 |
| 2016/0249008 | A1* | 8/2016 | Kitazawa | G02B 27/017 |
| 2016/0256771 | A1* | 9/2016 | Ekbia | G16H 20/30 |
| 2016/0300347 | A1* | 10/2016 | Dunn | G06T 7/60 |
| 2016/0317866 | A1* | 11/2016 | Fung | A63B 24/0087 |
| 2017/0365101 | A1* | 12/2017 | Samec | A61B 5/4088 |
| 2018/0263535 | A1* | 9/2018 | Cramer | A61B 5/1124 |
| 2019/0020530 | A1* | 1/2019 | Au | H04L 5/0057 |
| 2019/0042850 | A1 | 2/2019 | Jones et al. | |
| 2019/0371114 | A1* | 12/2019 | Diefenbach | A61B 5/0077 |
| 2020/0113511 | A1* | 4/2020 | Johnson | A61B 5/11 |
| 2020/0118164 | A1* | 4/2020 | DeFrank | G06Q 30/0269 |
| 2020/0185097 | A1* | 6/2020 | Orr | G09B 5/02 |
| 2020/0206503 | A1* | 7/2020 | Ganzer | A61N 1/025 |

OTHER PUBLICATIONS

Alison M. Cogan, MA, OTR/L, "Occupational Needs and Intervention Strategies for Military Personnel with Mild Traumatic Brain Injury and Persistent Post-Concussion Symptoms: A Review", *American Occupational Therapy Foundation,* OTJR: Occupation, Participation and Health, vol. 34, No. 3, pp. 150-159, 2014.
He et al., "Mask R-CNN", arXiv:1703.06870v3 ]cs.CV] Jan. 24, 2018.
Perneczky et al, "Impairment of activities of daily living requiring memory or complex reasoning as part of the MCI syndrome", *International Journal of Geriatric Psychiatry,* 2006, 21, 158-162.
Scherer et al., "Returning Service Members to Duty Following Mild Traumatic Brain Injury: Exploring the Use of Dual-Task and Multitask Assessment Methods", *Military Rehabilitation Special Issue,* American Physical Therapy Association, 2013, vol. 93, No. 9, pp. 1254-1267, Sep. 2013.
Weightman et al., "Further Development of the Assessment of Military Multitasking Performance: Iterative Reliability Testing", *PLOS ONE,* DOI:10.1371/journal.pone,0169104, Jan. 5, 2017.
Mihailidis Alex et al., The Coach prompting system to assist older adults with dementia through handwashing: An efficacy study, BMC Geriatrics, Biomed Central Ltd., Nov. 7, 2008, pp. 1-28, vol. 8, No. 1, London GB.
Rim Romdhane et al, Automatic Video Monitoring system for assessment of Alzheimer's Disease symptoms Auto-matic Video Monitoring system for assessment of Alzheimer's Disease symptoms, Journal of Nutrition Health and Aging, Jan. 1, 2011, p. 616747, retrieved from the internet: URL:https://hal.inria.fr/docs/00/61/67/47/PDF/JNHA-in_press.pdf.
Nguyen Thi-Hoa-Cuc et al, Recognition of Activities of Daily Living from Egocentric Videos Using Hands Detected by a Deep Convolutional Network, Big Data Analytics in the Social and Ubiquitous Context: 5th International Workshop on Modeling Social Media, MSM 2014, 5th International Workshop on Mining Ubiquitous and Social Environments, MUSE 2014 and First International Workshop on Machine LE, Jun. 6, 2018.
Rohrbach Marcus et al, Recognizing Fine-Grained and Composite Activities Using Hand-Centric Features and Script Data, International Journal of Computer Vision, Aug. 22, 2015, pp. 346-373, vol. 119, No. 3, Kluwer Academic Publishers, Norwell, US.
International Search Report for International Patent Application No. PCT/US2020/051167 dated Dec. 22, 2020.

* cited by examiner

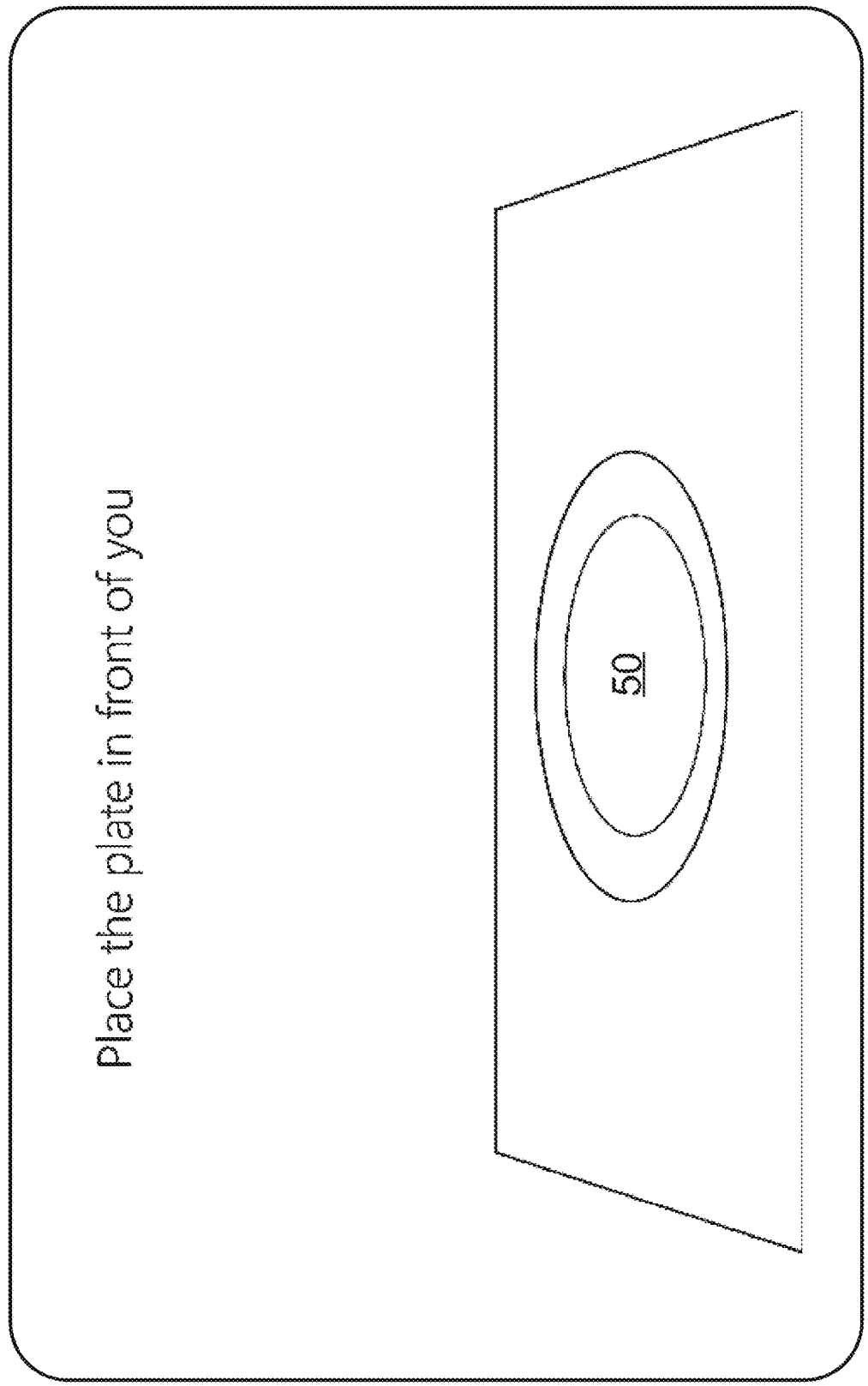

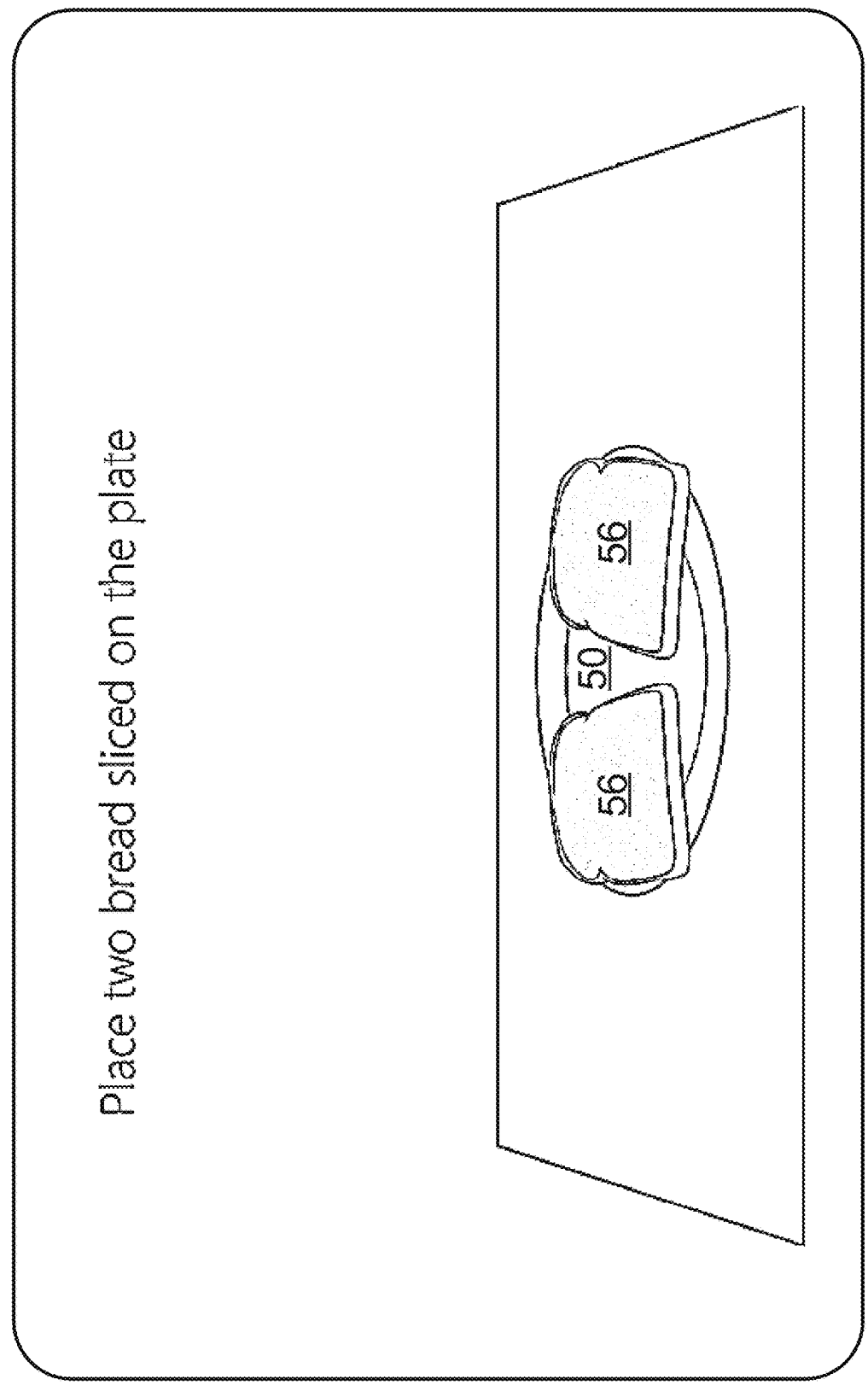

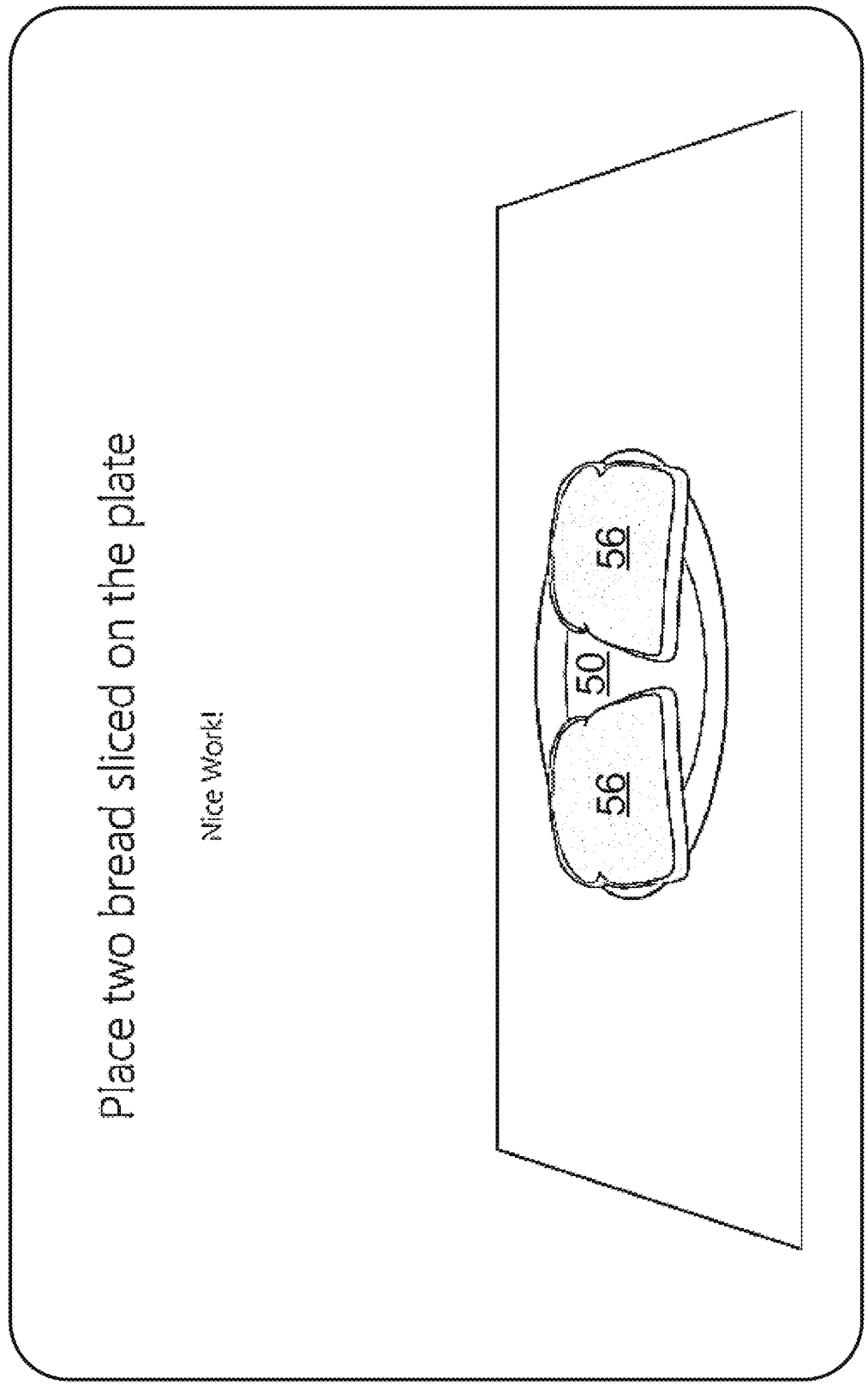

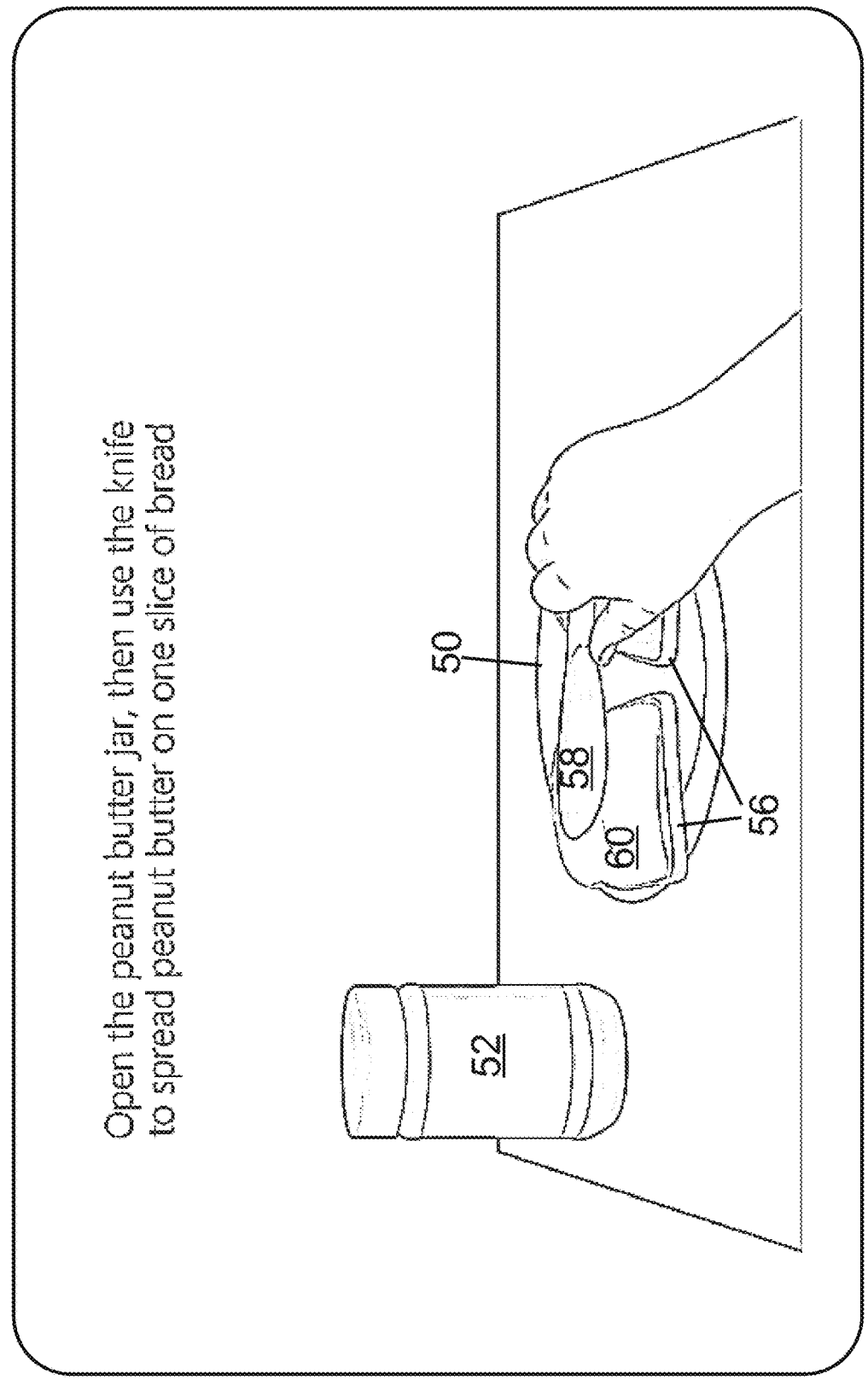

ACTIVITY ASSISTANCE SYSTEM

This application claims the benefit of U.S. Provisional Application No. 62/901,374 filed Sep. 17, 2019 and titled "ACTIVITY ASSISTANCE SYSTEM". U.S. Provisional Application No. 62/901,374 filed Sep. 17, 2019 and titled "ACTIVITY ASSISTANCE SYSTEM" is incorporated herein by reference in its entirety.

BACKGROUND

The following relates to the activity assistance arts, the rehabilitation therapy arts, activities of daily life (ADL) assistance arts, disability assessment for cognitive and/or motor disorders such as traumatic brain injury (TBI), Alzheimer's disease, brain lesions, stroke, or the like, and the like.

Rehabilitation therapy is a crucial recovery component for numerous medical conditions. For example, every year, more than 200,000 Traumatic Brain Injury (TBI) cases are reported in the United States alone. Many patients with TBI suffer cognitive impairment that affects their ability to interact with their environments and objects of daily living, preventing them from living independently. Approaches for TBI rehabilitation includes mirror therapy and therapist guided exercises. Since TBI is such a diffuse injury, these therapies only help some patients, and require therapist time which may be limited by insurance reimbursement or other practical considerations. More generally, rehabilitation therapy is commonly employed in persons suffering from agnosia (difficulty in processing sensory information) or apraxia (motor disorders hindering motor planning to perform tasks). Besides TBI, these conditions can be caused by conditions such as Alzheimer's disease, brain lesions, stroke, or so forth.

Certain improvements are disclosed herein.

BRIEF SUMMARY

In accordance with some illustrative embodiments disclosed herein, an activity assistance system includes a video camera arranged to acquire video of a person performing an activity, an output device configured to output human-perceptible prompts, and an electronic processor programmed to execute an activity script. The script comprises a sequence of steps choreographing the activity. The execution of each step includes presenting a prompt via the output device and detecting an event or sequence of events subsequent to the presenting of the prompt. Each event is detected by performing object detection on the video to detect one or more objects depicted in the video and applying one or more object-oriented image analysis functions to detect a spatial or temporal arrangement of one or more of the detected objects. Each event detection triggers an action comprising at least one of presenting a prompt via the output device and and/or going to another step of the activity script.

In accordance with some illustrative embodiments disclosed herein, an activity assistance method comprises: using a video camera, acquiring video of a person performing an activity; using an electronic processor, executing an activity script comprising a sequence of steps choreographing the activity wherein the execution of each step includes presenting a prompt via an output device and detecting an event or sequence of events subsequent to the presenting of the prompt, wherein each event is detected by performing object detection on the video to detect one or more objects depicted in the video and applying one or more object-oriented image analysis functions to detect a spatial or temporal arrangement of one or more of the detected objects; and responsive to each event detection, performing an action comprising at least one of presenting a prompt via the output device and and/or going to another step of the activity script.

In accordance with some illustrative embodiments disclosed herein, a non-transitory storage medium stores instructions readable and executable by an electronic processor to perform an activity assistance method comprising: receiving, from a video camera, video of a person performing an activity; executing an activity script comprising a sequence of steps choreographing the activity wherein the execution of each step includes presenting a prompt via an output device comprising one or more of a display and/or a loudspeaker and detecting an event or sequence of events subsequent to the presenting of the prompt, wherein each event is detected by performing object detection on the video to detect one or more objects depicted in the video and applying one or more object-oriented image analysis functions to detect a spatial or temporal arrangement of one or more of the detected objects; and responsive to each event detection, performing an action comprising at least one of presenting a prompt via the output device and and/or going to another step of the activity script.

In accordance with further embodiments and/or variants of the aforementioned embodiments, the disclosed activity assistance methods and systems may be employed for quantitative diagnosis of cognitive and/or motor disorders such as traumatic brain injury (TBI), Alzheimer's disease, brain lesions, stroke, or the like based on functional performance of tasks. In such embodiments or variants, the activity assistance system is programmed with task-oriented activities that allows individuals with (for example) mild to severe TBI to be assessed based on functional activity. Performance-based assessments in which the subject completes a complex task using real-world functional objects can be more sensitive to subtle cognitive impairment than traditional impairment-based measures. The activity assistance system suitably tracks the number of user errors, speed, sequencing ability, coordination, response times, and other meaningful metrics related to assessment of cognitive and/or motor skills status. Task difficulty and depth of feedback may be configurable and vary depending on the individual's injury and ability. Results of the assessment are suitably statistically analyzed and compiled in a performance report that informs the TBI (or other) diagnosis.

BRIEF DESCRIPTION OF THE DRAWINGS

Any quantitative dimensions shown in the drawing are to be understood as non-limiting illustrative examples. Unless otherwise indicated, the drawings are not to scale; if any aspect of the drawings is indicated as being to scale, the illustrated scale is to be understood as non-limiting illustrative example.

FIGS. 2A-15A diagrammatically show a progression of prompt dialog content presented by the activity assistance system of FIG. 1 for performing the activity of making a peanut butter & jelly (PB&J) sandwich.

FIGS. 2B-15B diagrammatically show images of a subject performing the activity of making a PB&J sandwich acquired by the video camera of the system of FIG. 1 at times corresponding to presentation by the system of the prompt dialog content of respective FIGS. 2A-15A.

DETAILED DESCRIPTION

Figure 1:
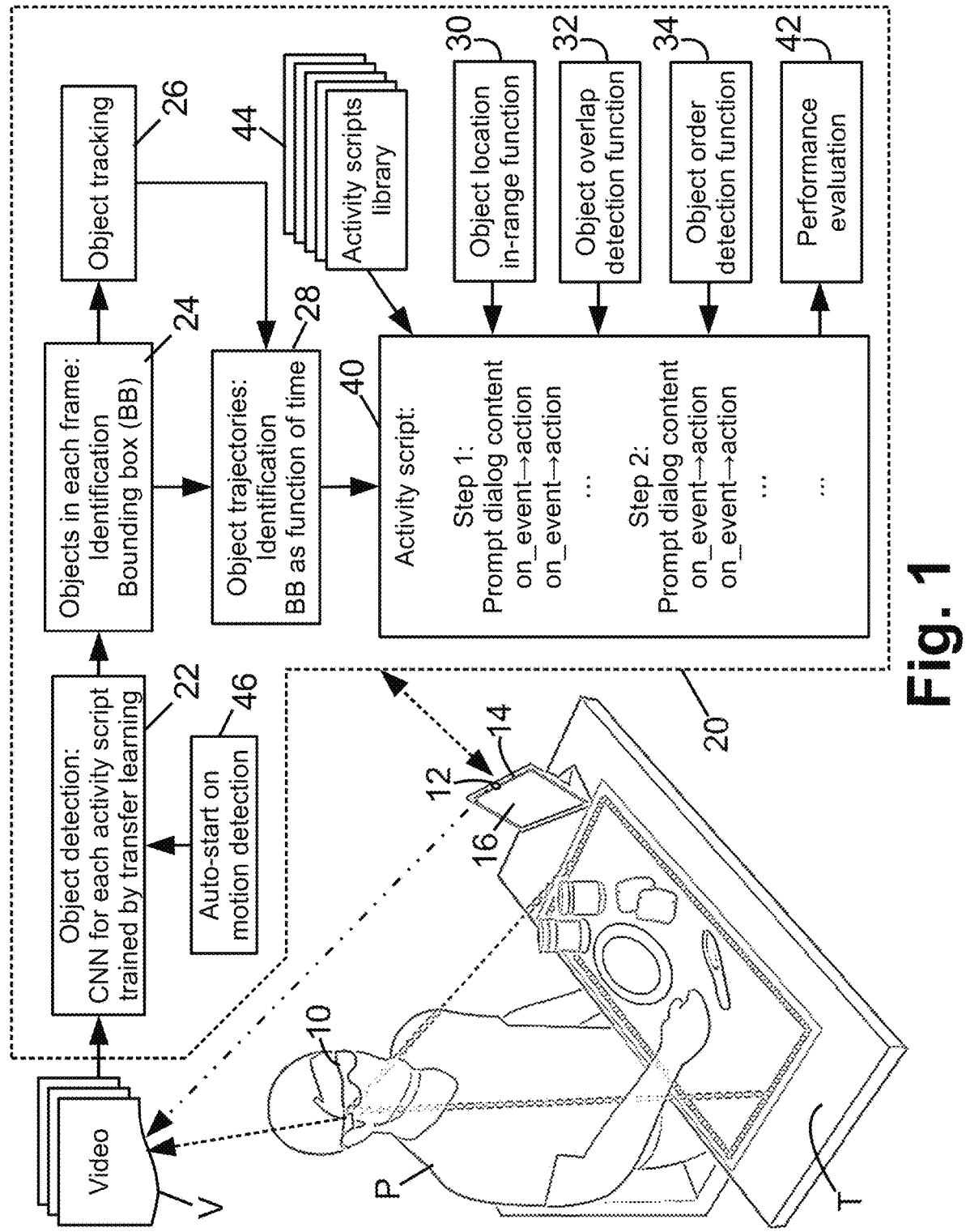
FIG. 1 diagrammatically shows an activity assistance system.

Physical and occupational therapists are commonly employed to guide a patient (or, more generally, a person) in performing various rehabilitation therapy activities. Many of these activities correspond to (or actually are) activities of daily living (ADLs) such as making a sandwich, brushing teeth, combing hair, or so forth. Since competence in performing various ADLs is essential for the patient to be able to live independently (or at least with limited assistance), ADLs performed under the guidance of the physical therapist are ideal rehabilitation therapy activities.

The usual approach of employing a physical therapist to guide a patient through rehabilitation therapy activities is problematic due to cost. Additionally, in cases in which the physical therapist cannot perform home visits, the rehabilitation therapy activities must be performed at a hospital or other centralized location. This may be difficult or impossible if the patient lacks adequate transportation. Even if the patient can come to the hospital, the unfamiliar setting may make it more difficult for the patient to perform an ADL. These limitations can lead to reduced therapy time, which reduces effectiveness of the therapy. Another difficulty with employing a physical therapist is that for certain ADLs, such as toileting, the patient may be uncomfortable having a physical therapist present while the patient performs the activity.

Another possible approach would be to employ a virtual reality (VR) system for performing the rehabilitation therapy activities. Commercial VR systems are relatively inexpensive, and can be programmed to simulate various rehabilitation therapy activities. However, VR systems may not provide sufficiently realistic feedback to the patient. The VR environment may differ significantly from the patient's home environment, which may hinder the patient's progress. Furthermore, sensory inputs may be imperfectly simulated by the VR system. In particular, tactile feedback in a VR system is typically crude or nonexistent. Tactile feedback is of importance for many ADLs. For example, a patient with agnosia may be more likely to correctly recognize an object if the patient has both visual and tactile sensory feedback. Using a VR system also usually involves wearing a headset and VR gloves with tactile sensors, again making the VR environment less than fully familiar and realistic to the patient. A further problem is that a patient who has difficulty with ADLs in general may have difficulty successfully putting VR gear on.

Disclosed herein are rehabilitation therapy systems (or, more generally, activity assistance systems) that can be deployed in the patient's home (or additionally or alternatively in a hospital, e.g. for the patient to receive additional therapy during in-patient stay), and which operate in the real world (rather than in VR) and preferably in the patient's home and using the patient's own objects. The disclosed approaches leverage the fact that performing most ADLs require manipulation of, or contact with, a small set of objects. For example, the ADL of brushing teeth may involve as few as four objects: a toothbrush, toothpaste, a faucet handle, and a water stream (which comes into existence when the faucet handle is turned on). The ADL of combing hair may involve only two items: a comb or brush, and the patient's head. The disclosed approaches further leverage the fact that, in performing most ADLs, there is a small and discrete number of mistakes the patient is likely to make. For example, a patient with agnosia is most likely to make a mistake in which one object of the small set of objects is mistaken for another object of that small set. If the set size is five objects then there are only $$\binom{5}{2} = 10$$

theoretically possible ways of confusing two objects, some of which may be improbable or impossible in a given ADL. For example, in the case of the tooth brushing ADL having four objects, there are theoretically six possible object confusion mistakes, but by far the most probable one is confusing the toothbrush and toothpaste. For a patient with apraxia, most common mistakes are to mis-order objects, or perform a sequence of operations in the wrong order. For five objects, there are 5!=120 possible orders, but again many of these may be unlikely in a given ADL, so that there is a limited number of ways ordering mistakes can be made for a particular ADL. Yet a further insight is that a typical ADL is sequential in nature, with only a relatively small number of well-defined steps and little or no branching. For example, the brushing teeth ADL may entail the sequential steps of: pick up toothbrush; place toothbrush under water briefly; pick up toothpaste; apply toothpaste to toothbrush; brush teeth using toothbrush; place toothbrush under water briefly; and replace toothbrush.

With reference to FIG. 1, based on these insights, an illustrative activity assistance system for use by a patient P (or, more generally, person receiving the assistance) uses video camera-based object recognition to identify the objects involved in the ADL (or, more generally, the rehabilitation therapy activity, or even more generally, the activity) in video V captured by the video camera. The video camera may, for example, be a video camera of smart glasses 10 worn by the patient, or in an alternative embodiment the video camera may be a webcam 12 of a notebook computer 14 that hosts the rehabilitation therapy system or an external webcam that is mounted in the room to view the therapy setting. The smart glasses 10 include a built-in video camera that captures images from the vantage of the patient P wearing the smart glasses 10, and a transparent display mounted on the lenses of the smart glasses 10 (or, alternatively, the display of the smart glasses 10 may be an opaque display positioned at a perimeter of the lenses). It will also be appreciated that the video camera may employ another imaging modality besides visual, such as LIDAR, infrared imaging, or so forth. The illustrative rehabilitation therapy system further includes at least one output device for presenting prompts for performing the ADL to the patient, or for presenting other information to the patient. The at least one output device may include the mentioned display of the smart glasses 10, and/or a display 16 of the notebook computer 14, and/or a loudspeaker of the smart glasses 10 or of the notebook computer 14. By way of non-limiting illustration, a prompt may be presented as: natural language audio (e.g., using speech synthesis played on a loudspeaker); natural language text displayed on the display 16 of the computer 14; natural language text superimposed on the patient's field of view (FOV) via the AR display of the smart glasses 10; an image, graphic, or the like displayed on the display 16 of the computer 14; an image, graphic, or the like superimposed on the patient's field of view (FOV) via the AR display of the smart glasses 10; various combinations thereof; and/or so forth.

The illustrative notebook computer 14 is programmed to perform a computerized rehabilitation therapy method 20 diagrammatically shown in FIG. 1 by way of a block diagram. Particularly, the computer 14 is programmed to perform: object detection 22 which identifies objects in frames of the video V and delineates the location of each object in the frame by (in the embodiment of FIG. 1) a bounding box (BB) 24; and object tracking 26 across successive image frames, thereby generating object trajectories 28 suitably represented as the BB of each identified object as a function of time. The computer 14 is further programmed to perform object-oriented image analysis functions, such as (in the illustrative example) an object location in-range function 30 (detecting whether an object is within a defined spatial range), an object overlap detection function 32 (detecting whether two objects overlap in space from the vantage of the video camera), and an object order detection function 34. These object-oriented image analysis functions 30, 32, 34 provide the ability to detect a wide range of errors in manipulating objects during performance of a typical ADL, particularly errors of the types typically made by patients suffering from agnosia or apraxia.

To provide rehabilitation therapy for a particular ADL, the computerized rehabilitation therapy method 20 further includes executing an activity script 40 by the computer 14. The activity script 40 choreographs an ordered sequence of steps making up the ADL. The execution of each step of the sequence includes presenting a human-perceptible prompt and detecting an event or sequence of events subsequent to the presenting of the prompt. The detected events trigger actions, and hence are referred to as on_event→action responses. (It is noted that while the detect event is typically a positive event which actually occurs, the event of some on_event→action responses may be a negative event, that is, an event which does not occur within a specified time frame. For example, if the patient is asked to pick up an object, an on_event→action response may comprise the event of failing to detect the patient picking up the object in, for example, 5 seconds, and the resulting action may for example be to send a new, perhaps more detailed, prompt instructing the patient to pick up the object). As already described, the prompts may be presented as natural language audio, natural language text, images, graphics, various combinations thereof, and/or so forth. For example, if the first step calls for the patient P to place a set of objects into a particular order, then the prompt may be the natural language spoken and/or displayed text "Please place the objects shown into the order shown" together with an image or graphical depiction of the objects in the desired order presented as AR content via the smart glasses 10 or as a 2D image shown on the display 16.

Each on_event→action response is triggered by an event detected by performing the object detection 22 on the video V to detect one or more objects depicted in the video V and applying at least one of the one or more object-oriented image analysis functions 30, 32, 34 to detect a spatial or temporal arrangement of one or more of the detected objects. The detection of an event triggers an action such as providing an additional prompt, and/or going to another step of the activity script 40. To continue the immediate example, if the object order detection function 34 detects that the objects are laid out by the patient P in the wrong order (the "on_event") then the action part of the response may be to display a further prompt indicating the error and asking the patient P to correct the error. On the other hand, if the object order detection function 34 detects that the objects are laid out by the patient P in the correct order (the "on_event") then the action part of the response may be to display a further prompt congratulating the patient P for this success.

In general, a sequence of on_event→action responses may occur, as driven by the events observed in the video V using the object-oriented image analysis functions 30, 32, 34. For example, the patient P may initially place the objects in the wrong order (first "on_event") triggering the corrective prompt response; then, the patient P may correct the ordering of the objects (second "on_event") triggering the congratulatory prompt response. It is also contemplated for an on_event→action response to entail recursively returning to a previous step. For example, the first step may be for the patient to place the objects on the table T, and the second step may be for the patient to order the objects in a particular order. If, at the second step, the patient knocks an object off the table T (an "on_event" suitably detected by the object location in-range function 30 not being located anywhere in the video frame) then the response may be to go back to the first step. Furthermore, for a more complex ADL, an on_event→action response may produce a branching in the choreographed flow of the ADL, e.g. of the form "on_event1→goto step x"; "on_event2→goto step y".

Upon completion of the activity script 40 (and, hence, completion of the ADL choreographed by that script 40), a performance evaluation 42 preferably analyzes the performance of the patient P. This analysis can, for example, count the total number of "on_event→action" responses that correspond to correct actions by the patient P versus a count of the total number of "on_event→action" responses that correspond to incorrect actions by the patient P. Optionally, this may be further broken down, e.g. distinguishing between "on_event→action" responses that correspond to incorrect object identification versus "on_event→action" responses that correspond to incorrect object ordering. Other performance metrics can be employed, such as total completion time, optionally broken down into completion times for various different steps.

Optionally, the video V, or portions thereof, may be saved on a non-transitory storage medium for later review by the patient's physician. Such recordation, if done at all, should be done in compliance with applicable patient privacy regulations and only with the consent of the patient P or the patient's legal guardian.

The illustrative rehabilitation therapy system includes a library 44 of activity scripts for different ADLs. By way of non-limiting illustration, the library 44 may include activity scripts correlating ADLs such as making a sandwich, brushing teeth, taking one or more medications, combing hair, toileting, trash removal, cooking tasks, grocery shopping tasks, ironing, pumpkin carving, present wrapping, picture framing, or so forth. Advantageously, a wide range of different ADLs can be supported merely by constructing a suitable script for each ADL. Constructing a script entails identifying the sequence of steps making up the ADL, and for each event adding an appropriate prompt and appropriate "on_event→action" responses. The prompts can be synthesized audio speech, textual natural language content presented on a display, and/or images or graphical representations. For example, a prompt asking the person P to arrange a set of objects in a specified order can include an image of the objects in that order, or can include a graphical representation of the objects in that order (for example, constructed using a the Blender modeling toolset (available from the Blender Foundation). In one suitable embodiment, MATLAB or Python scripts are programmed, including a master script that calls on selected activities. The activities have information regarding the sequences, prompts, and error/correct responses. Each step in the sequence is linked to one or more object-oriented image analysis functions 30, 32, 34. Each step is iterated through in the master script and, based on the type of action detected, the master script determines the effect. This allows the system to generalize to many activities. The object-oriented image analysis functions 30, 32, 34 are typically custom built, using matrix operations on the bounding boxes 24 that are generated from the CNN 22. For the object location in-range function 30, the center of the bounding box is measured from the edges of the image in pixels. A confidence bound is set to allow for some error in positioning. A suitable boundary such as a mat (see, e.g. FIG. 2B) can also be tracked and used to reference the object locations based on the bounding box. For the object overlap detection function 32, the area of overlap between bounding boxes is calculated as well as the distances between corners to calculate overlap. For the object order detection function 34, each bounding box is linked to an object, so the corner of each bounding box is used to determine the ordering of objects. The x-axis location, in pixels, is used. These are merely illustrative examples of object-oriented image analysis functions. As still yet another non-limiting example (not shown), an object touching operation can be applied to determine whether the user's hand is touching/holding an object. This suitably uses similar logic to the object overlap detection function 32, but does so with a model that detects the objects and a model that detect the user's hand. Both models run in parallel and use similar architectures for detection and bounding box generation. The CNN 22 can be a standard off-the-shelf neural network, and is optionally retrained with task-specific images using transfer learning. To maximize accuracy for an activity script, the CNN 22 is preferably trained to detect objects of the set of objects involved in the script. Alternatively, the rehabilitation therapy system may be designed to provide rehabilitation therapy assistance for a single ADL, in which case only a single activity script is needed and the library 44 is suitably omitted.

The illustrative rehabilitation therapy system is triggered by an auto-start function 46 which monitors the webcam 12 and starts the video acquisition and starts running the script 40 upon detection of motion by the webcam 12. Advantageously, this allows the patient P to start using the illustrative rehabilitation therapy system without taking any affirmative action other than sitting down at the table T. Other auto-start triggers are contemplated, such as starting the computer 14 or the smart glasses 10 (a suitable approach if the computer or smart glasses are only used in the rehabilitation therapy system), performing facial recognition on video acquired by the webcam to detect the face of the patient P, or so forth. Instead of an autostart, the rehabilitation therapy system can be manually started by bringing up a rehabilitation therapy application program on the computer 14 (a suitable approach if, for example, the person P has in-home assistance, or is capable of reliably taking these actions).

The illustrative rehabilitation therapy system is merely an example, and numerous variants are contemplated. For example, the system could include only the smart glasses 10. In this embodiment, the video camera of the smart glasses 10 would serve to provide the video V and the AR display and/or loudspeaker of the smart glasses 10 would present the prompts. Conversely, the system could include only the computer 14. In this embodiment, the webcam 12 would serve to provide the video V and the display 16 and/or loudspeaker of the computer 14 would present the prompts. In the case of a task involving manipulation of objects on a table, the webcam 12 may be modified as compared with the webcam of a commercial laptop or notebook computer in order to have its field of view (FOV) angled downward to image a surface on which the laptop or notebook computer is disposed when the display 16 is oriented to be viewed by the person P. (By comparison, the webcam of a commercial laptop or notebook computer is typically angled generally forward so as to capture the face of the person P when the person P is viewing the display 16). Advantageously, the laptop or notebook computer with the thusly modified webcam provides a portable, single-component system for implementing the activity assistance system, as in this embodiment the smart glasses 10 could be omitted. Further, the illustrative notebook computer 14 could be replaced by a desktop computer, mobile device (e.g. a cellphone or tablet computer, preferably mounted in a dock), and/or so forth. In other embodiments, other hardware arrangements may be used. For example, to assist in a tooth brushing ADL, the video camera may optionally be mounted on the bathroom wall and the display may be integrated into a bathroom mirror. The illustrative object-oriented image analysis functions 30, 32, 34 can be replaced and/or augmented by other object-oriented image analysis functions, such as an in-front-of detection function that detects when an object A is in front of an object B, or a reciprocation detection function that detects when an object is moving back-and-forth (useful, for example, in constructing a tooth brushing ADL script).

The rehabilitation therapy system comprises, in part, an electronic processor programmed to perform the computerized rehabilitation therapy method 20. The electronic processor may include the electronic processor of the computer 14 and/or the electronic processor of the smart glasses 10. Optionally, some portions of the computerized rehabilitation therapy method 20 may be performed by a cloud computing resource comprising ad hoc connected Internet-based server computers. The computerized rehabilitation therapy method 20 is suitably embodied as a non-transitory storage medium storing instructions which are readable and executable by such a processor to perform the computerized rehabilitation therapy method 20 in conjunction with a video camera for acquiring the video V and an output device for presenting the prompts. By way of non-limiting illustrative example, the non-transitory storage medium may comprise a hard disk or other magnetic storage medium, an optical disk or other optical storage medium, a solid state drive (SSD) or other electronic storage medium, or various combinations thereof.

Advantageously, the disclosed rehabilitation therapy systems can be set up in the patient's home with very limited hardware (e.g., the notebook computer 14 and/or the smart glasses 10 in the illustrative example). The object detector 22 may comprise an available artificial intelligence (AI) based object recognition module such as ResNet-50 which employs a convolutional neural network (CNN) trained on images from the ImageNet database and using a YOLO (You Only Look Once) framework in which the entire image is processed once, as a whole, by the CNN. While standard video runs at 30 frames/second (30 fps), for the disclosed rehabilitation therapy systems, the frame rate can optionally be lowered to as low as a few frames per second, which can facilitate object recognition processing performed on a frame-by-frame basis as each frame is acquired. Furthermore, in a typical ADL the patient P handles a small, finite number of discrete objects, usually 5-10 objects or less. For this closed universe of 5-10 objects, transfer learning can be used to tailor the CNN to the specific objects involved in the activity, and to further enhance accuracy. An off-the-shelf object recognition CNN may not be trained to recognize the objects involved in the activity, or may only be trained to recognize generic objects. For example, an off-the-shelf CNN that is trained to recognize a generic "jar" is unsuitable for a peanut butter-and-jelly sandwich making task in which the peanut butter jar and the jelly jar must be differentiated. By using a color video camera, color features can also be employed in the object recognition. As a consequence, it is expected that object recognition accuracy of close to 100% can be readily achieved for the objects handled by the patient P in most ADLs, along with high concomitant rejection (i.e. ignoring) of non-relevant objects that are not involved in the activity of the activity script.

In general, the rehabilitation therapy system includes a video camera (e.g., the video camera of the smart glasses 10, or the webcam 12 of the computer 14) arranged to acquire video V of the person P performing an activity (typically an ADL); an output device configured to output human-perceptible prompts (e.g., the display 16 of the computer 14, and/or the display of the smart glasses 10, and/or a loudspeaker of the computer 14, and/or a loudspeaker of the smart glasses 10; and an electronic processor (e.g., the electronic processor of the computer 14 and/or the electronic processor of the smart glasses 10 and/or electronic processors of an Internet-based cloud computing resource). The electronic processor is programmed to execute the activity script 40 comprising a sequence of steps choreographing the activity. The execution of each step includes presenting a prompt via the output device and detecting an event or sequence of events subsequent to the presenting of the prompt. Each event is detected by performing object recognition on the video V to detect one or more objects depicted in the video (e.g., via operations 22, 26) and applying one or more object-oriented image analysis functions 30, 32, 34 to detect a spatial or temporal arrangement of one or more of the detected objects. Each event detection triggers an action comprising at least one of presenting a prompt via the output device and and/or going to another step of the activity script 40.

With reference now to FIGS. 2A-15A and FIGS. 2B-15B, an illustrative rehabilitation therapy method suitably performed by the rehabilitation therapy system of FIG. 1 is described. The illustrative example executes an activity script for the ADL of making a peanut butter and jelly (PB & J) sandwich. In the examples, the video camera of the smart glasses 10 is used to acquire the video V, the electronic processor of the computer 14 executes the computerized rehabilitation therapy method 20, and the display 16 of the computer 14 is used as the output device. To illustrate the method, FIGS. 2A-15A illustrate the prompts presented on the display 16 for successive steps of the PB & J sandwich-making ADL, and corresponding FIGS. 2B-15B show a representative frame of the video V acquired during the execution of the respective steps of the PB & J sandwich-making activity script. The prompts for the PB & J sandwich-making ADL shown in FIGS. 2A-15A include graphical representations of the following objects: a plate 50, a jar of peanut butter (PB) 52, a jar of jelly or jam 54, bread 56 (one or two slices in any given graphical representation), a knife 58, a spread of PB 60, and a spread of jelly 62. The corresponding video frames of FIGS. 2B-15B show the corresponding detected objects in the images: a detected plate 50$i$, a detected jar of peanut butter (PB) 52$i$, a detected jar of jelly or jam 54$i$, detected bread 56$i$ (one or two detected slices in any video frame), a detected knife 58$i$, a detected spread of PB 60$i$, and a detected spread of jelly 62$i$. It should be noted that the reference symbols 50, 52, 54, 56, 58, 60, 62 are superimposed on the graphical representation and are not part of the graphical representations shown in FIGS. 2A-14A. Likewise, the reference symbols 50$i$, 52$i$, 54$i$, 56$i$, 58$i$, 60$i$, 62$i$ are superimposed on the image frames of FIGS. 2B-14B and are not part of actual image frames.

Figure 2A:
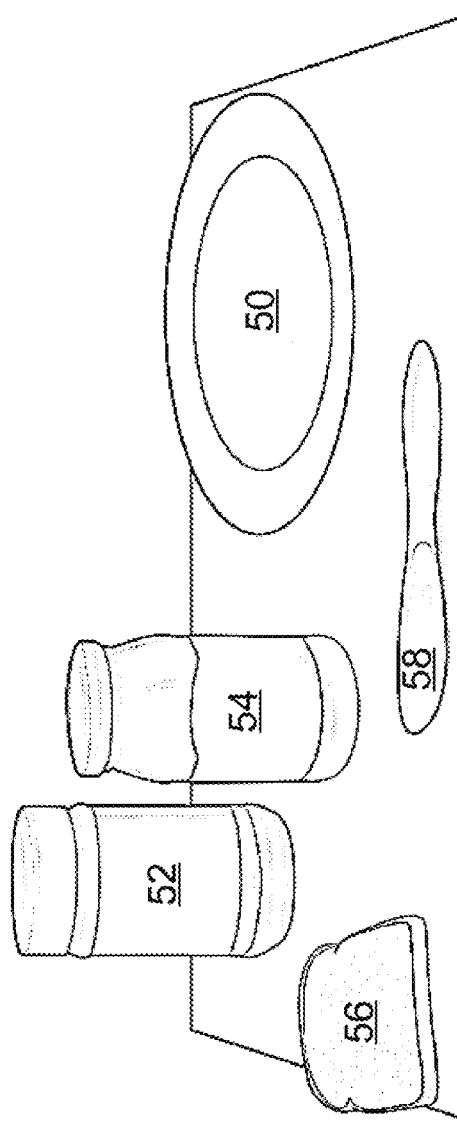
Figure 2B:
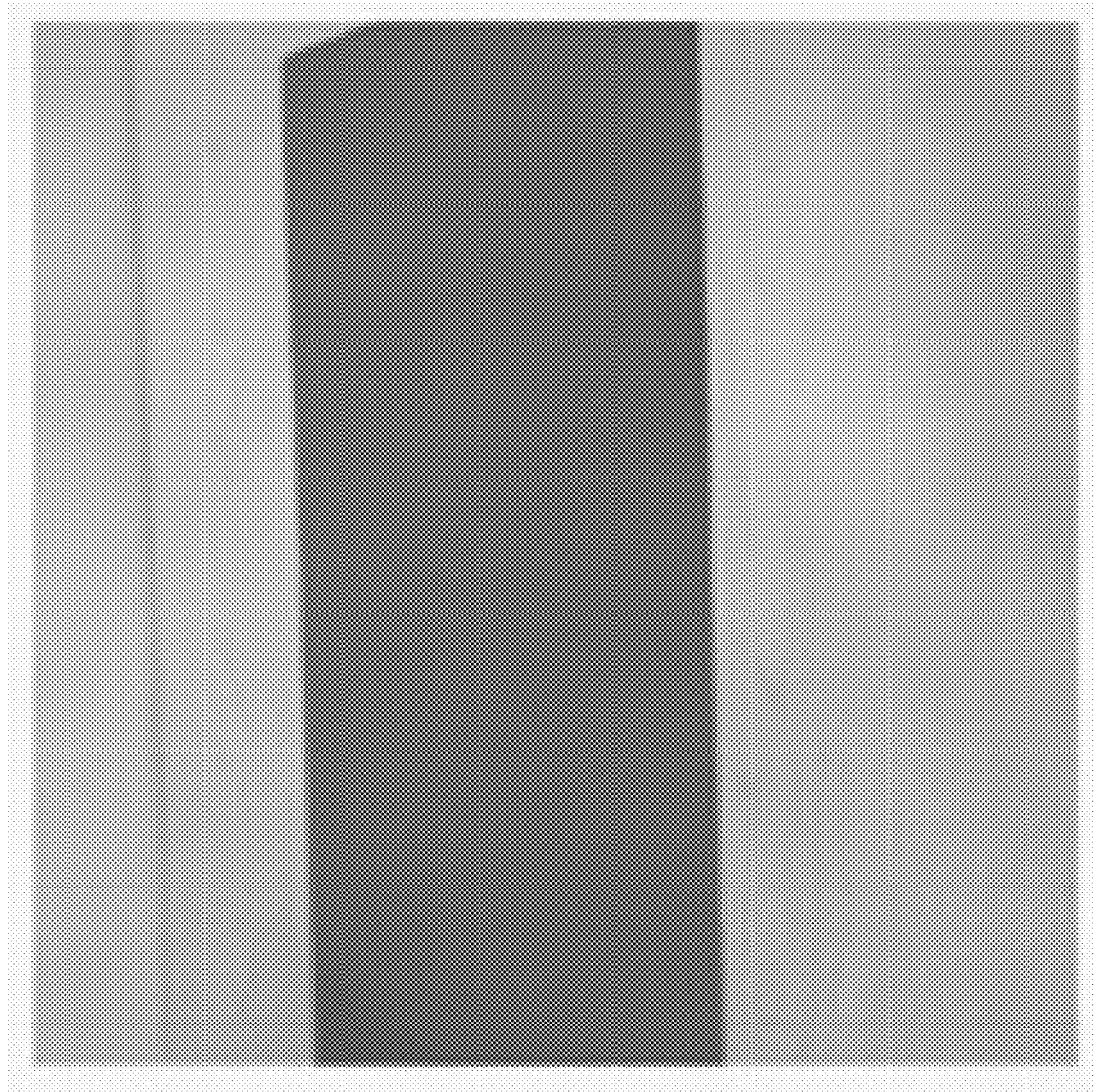
Figure 3A:
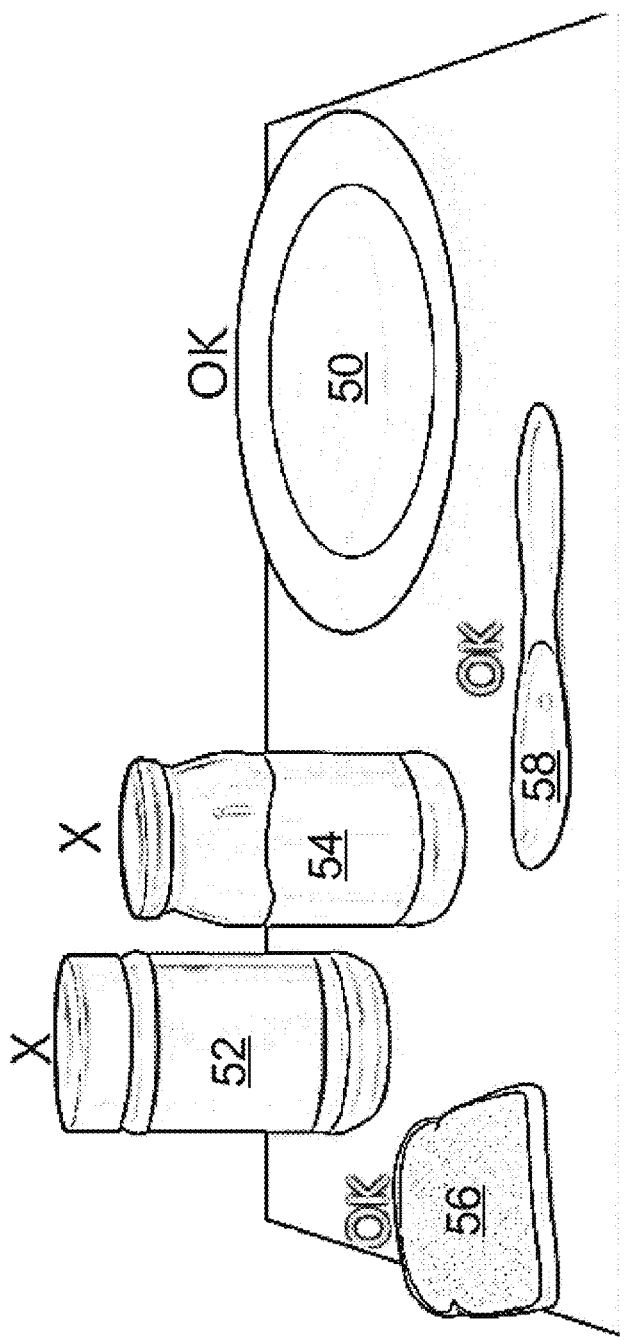
Figure 3B:
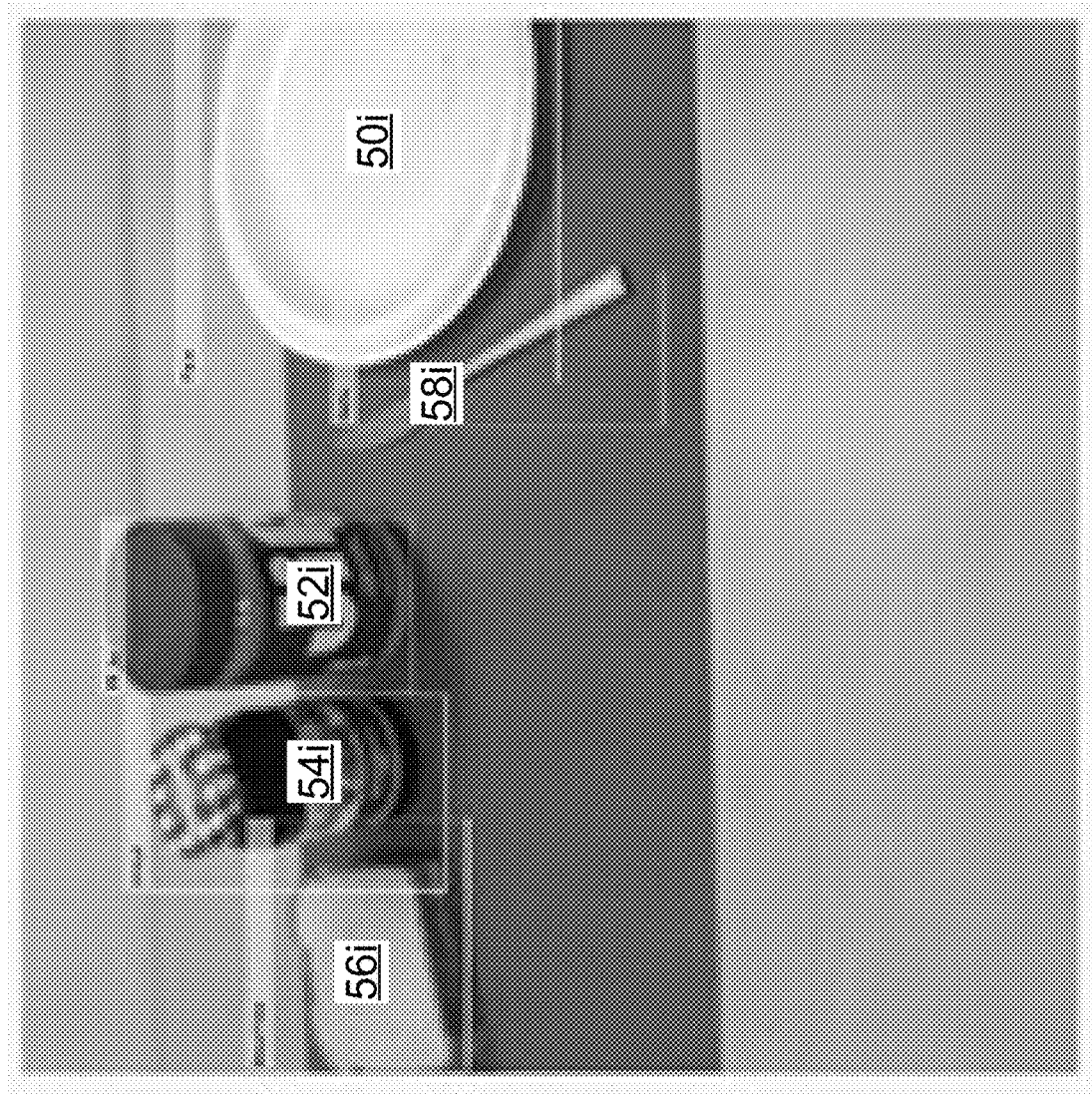
Figure 4A:
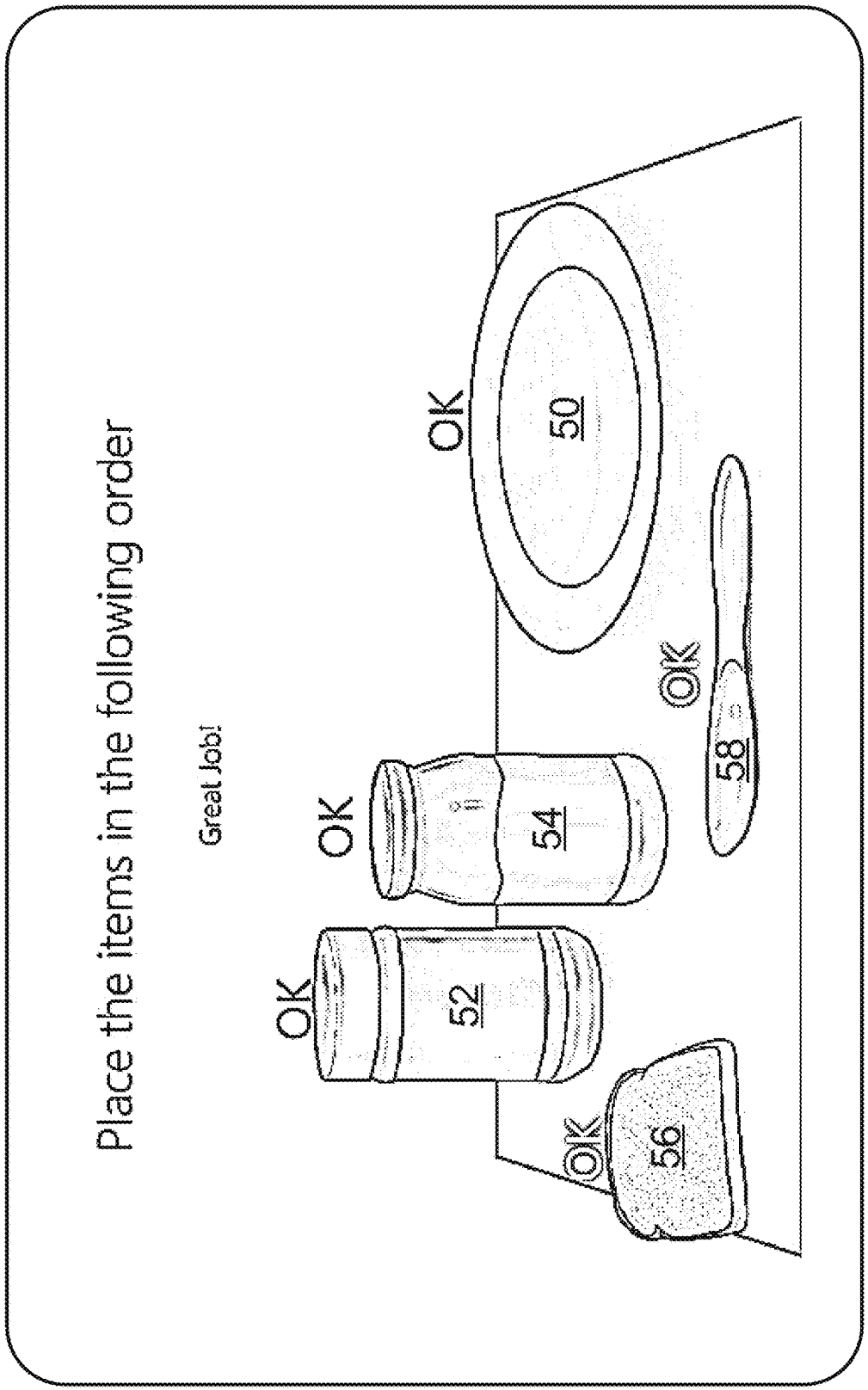
Figure 4B:
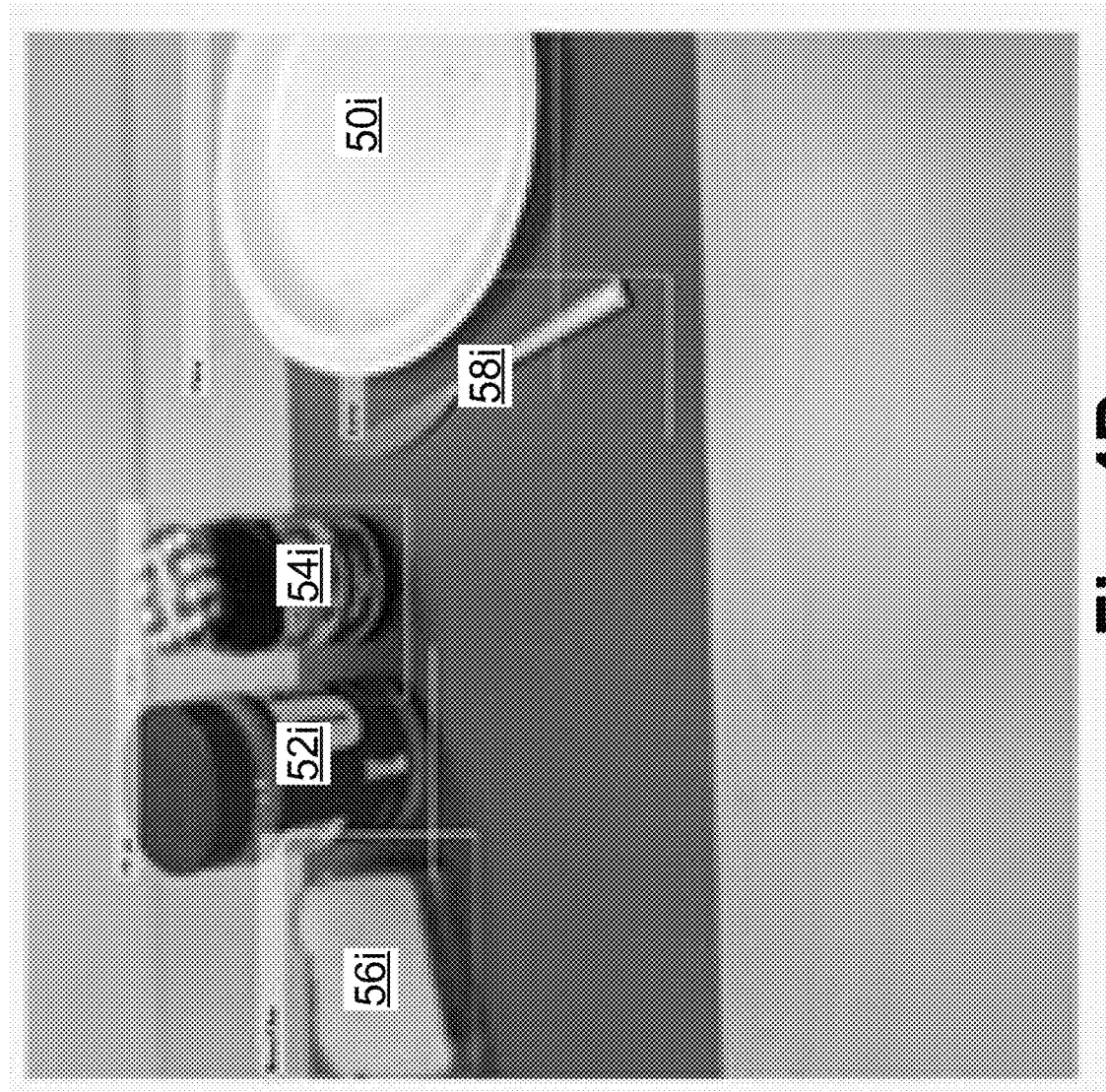

FIG. 2A illustrates an initial prompt asking the patient to place items 50, 52, 54, 56, 58 onto the table in the graphically represented order. The video frame of corresponding FIG. 2B acquired at the time the prompt of FIG. 2A is presented shows that at this point, the patient has not placed any items onto the table. As seen in FIG. 3B, the patient initially places the items on the table, but in the incorrect order as the peanut butter 52$i$ and jelly 54$i$ are reversed compared with the order of the peanut butter 52 and jelly 54 shown in the prompt of FIG. 2A. The object order detection function 34 detects this incorrect order, and the responsive action is to display the prompt shown in FIG. 3A, which identifies the error by the text: "The order seems a little off. Try moving the items marked with a red X", and by the indicated "X" marking in the graphical representation of the prompt of FIG. 3A. FIG. 4B shows the image frame after the patient has corrected the ordering by switching the peanut butter and jelly. The object order detection function 34 detects this now correct order, and the responsive action is to display the congratulatory prompt shown in FIG. 4A which includes the text "Great job!" and to move to the next step of the activity script.

Figure 5B:
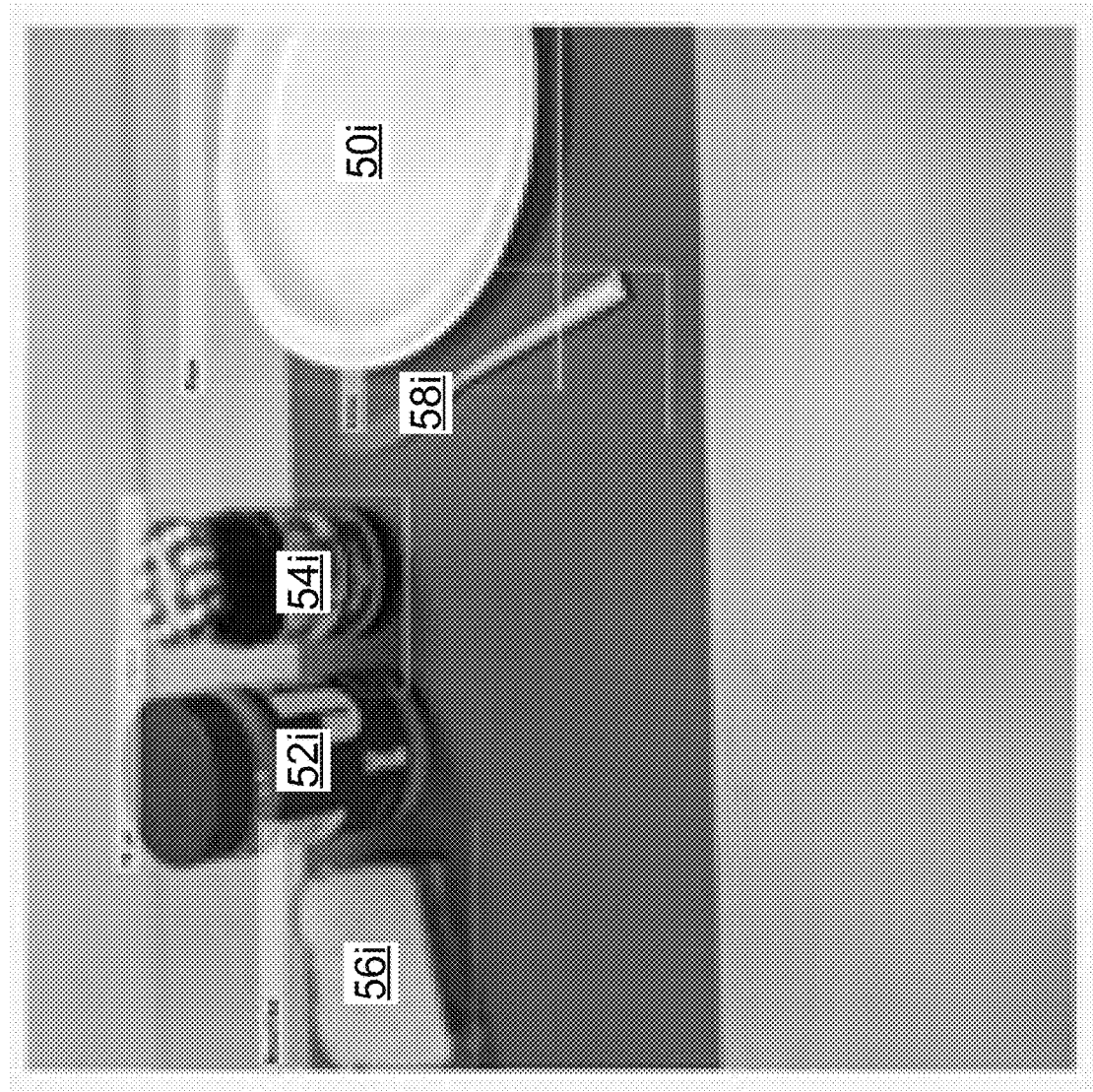
Figure 6A:
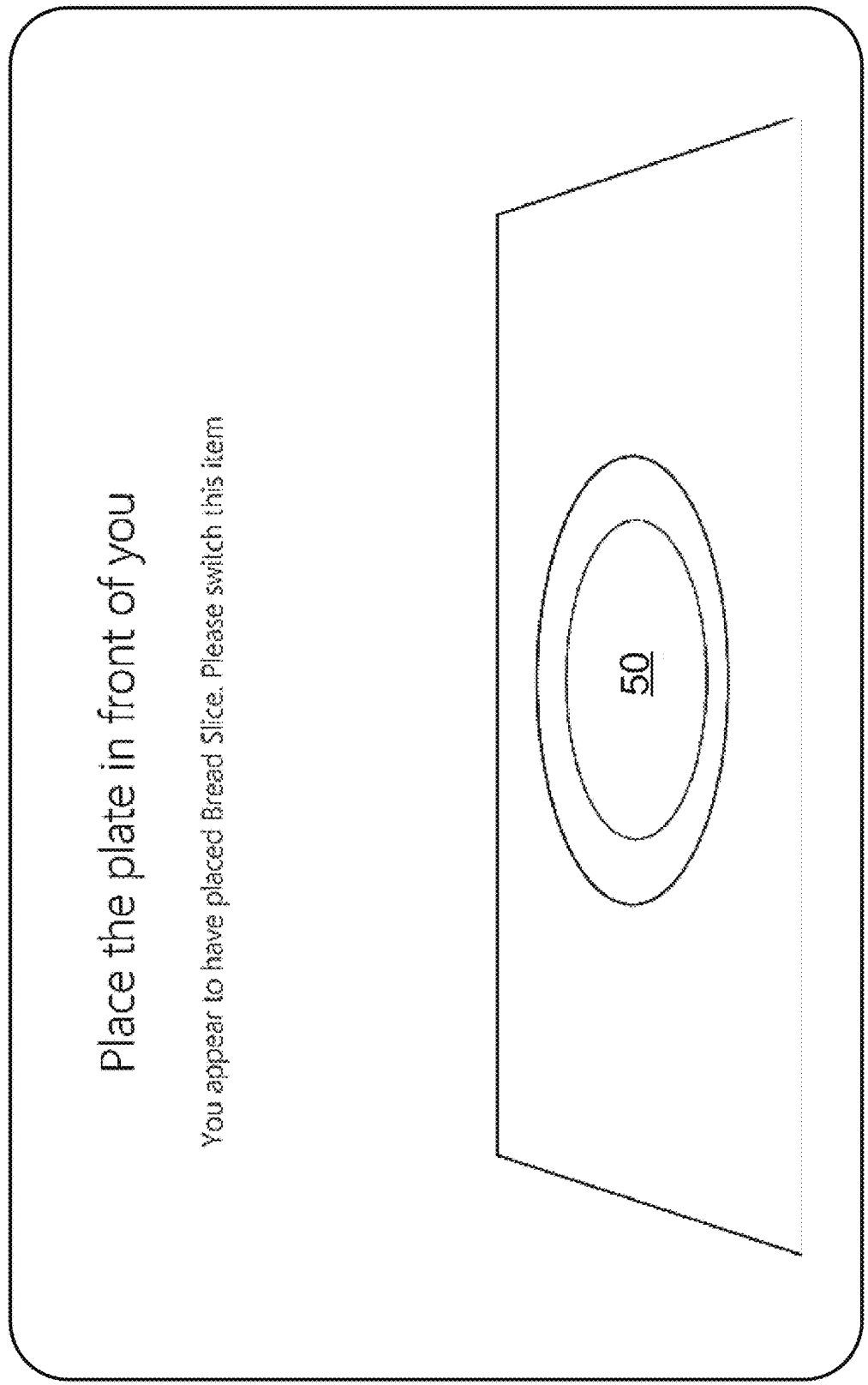
Figure 6B:
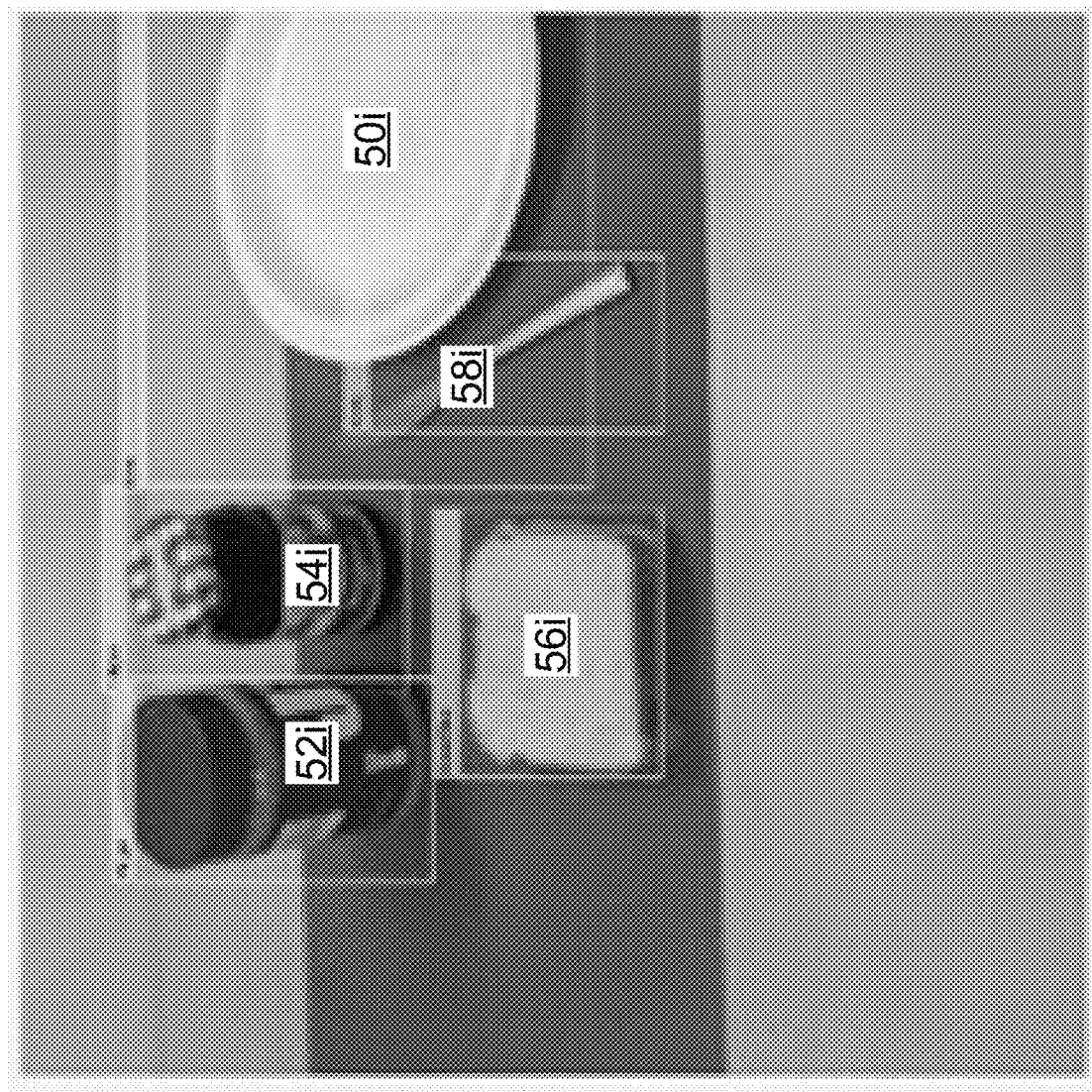
Figure 7A:
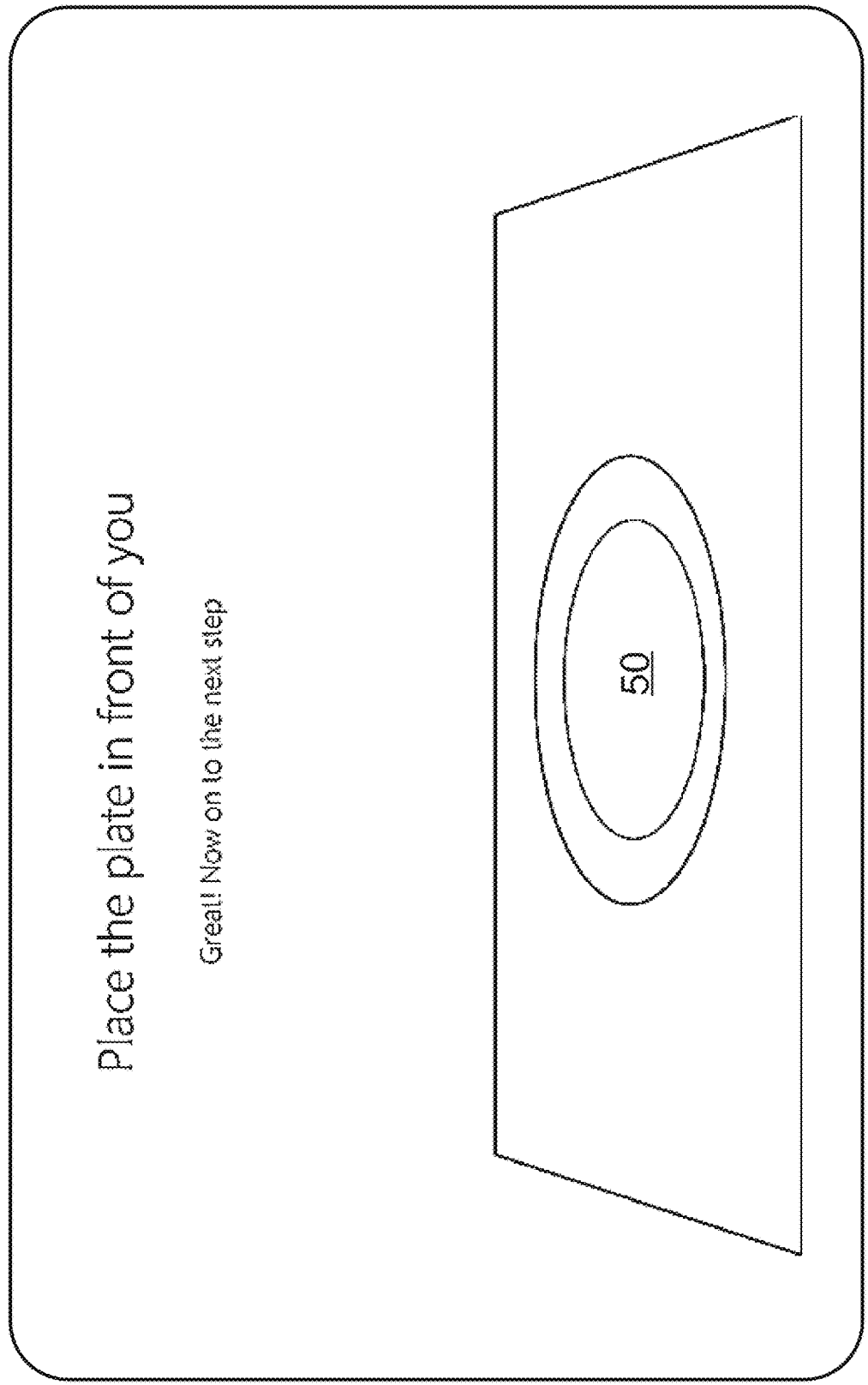
Figure 7B:
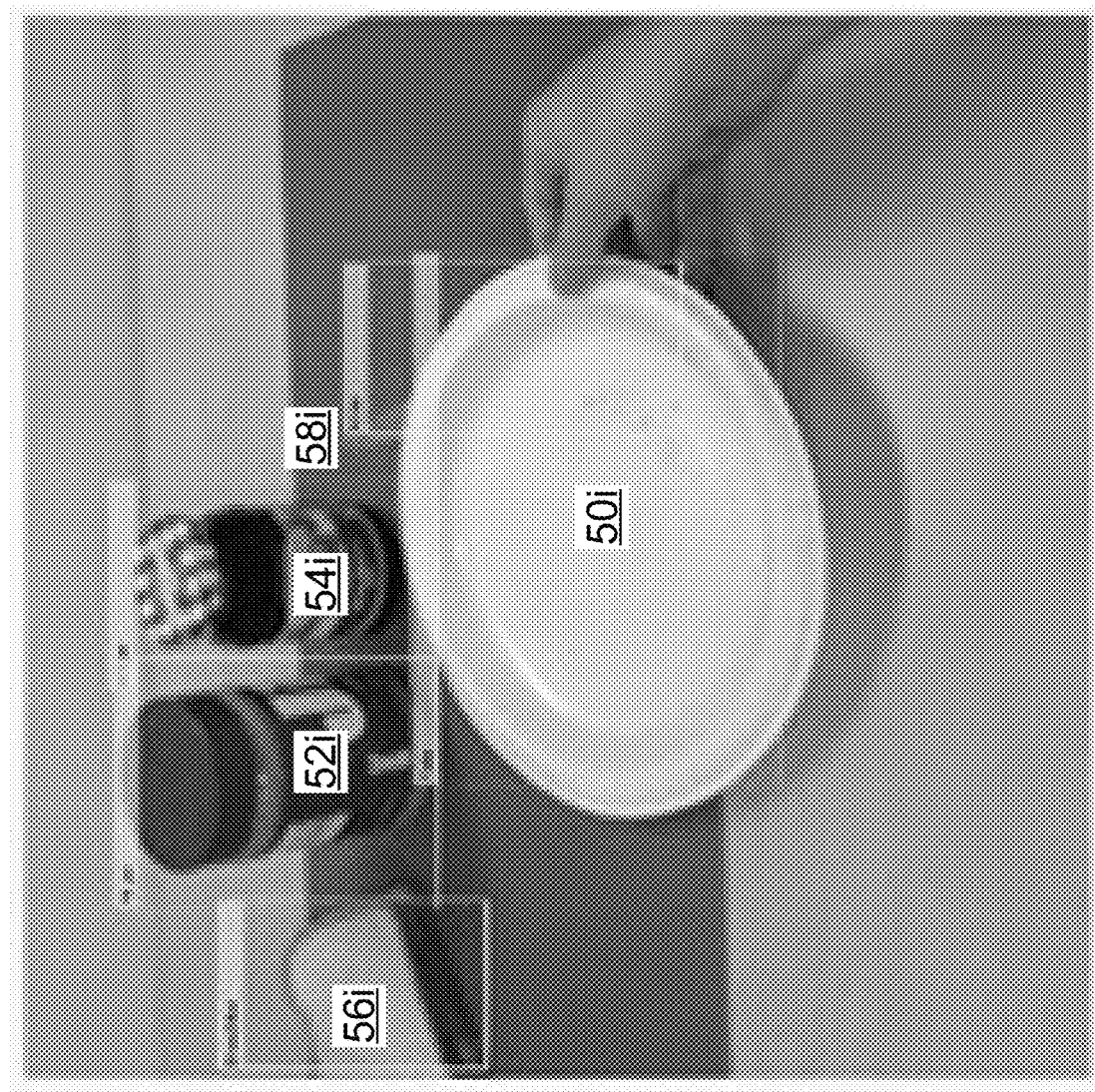

The next step of the PB & J sandwich making activity script presents the prompt shown in FIG. 5A, which asks the patient to "Place the plate in front of you" with the prompt further including a graphical representation of the plate 50 in the specified location at the center of the table (i.e., "in front of you"). As seen in FIG. 5B, at the time the prompt of FIG. 5A is initially presented the video frame still shows the arrangement achieved by the patient at FIG. 4B. As seen in FIG. 6B, the patient erroneously places the bread 56$i$ at the specified location, rather than the plate 50$i$. The object location in-range function 30 detects the error that the bread is at the specified location, rather than the specified plate. FIG. 6A shows the prompt that is presented response to this error detection, which states "You appear to have placed the Bread Slice. Please switch this item." The prompt also retains the graphical representation of the prompt of FIG. 5A showing the plate 50 at the specified location. FIG. 7B shows the image frame after the patient corrects the error by switching the plate and the bread. This correct placement of the plate 50$i$ in the specified location ("in front of you") is detected by the object location in-range function 30, triggering the responsive congratulatory prompt shown in FIG. 7A including the text "Great! Now on to the next step", along with triggering going to the next step of the activity script.

Figure 8B:
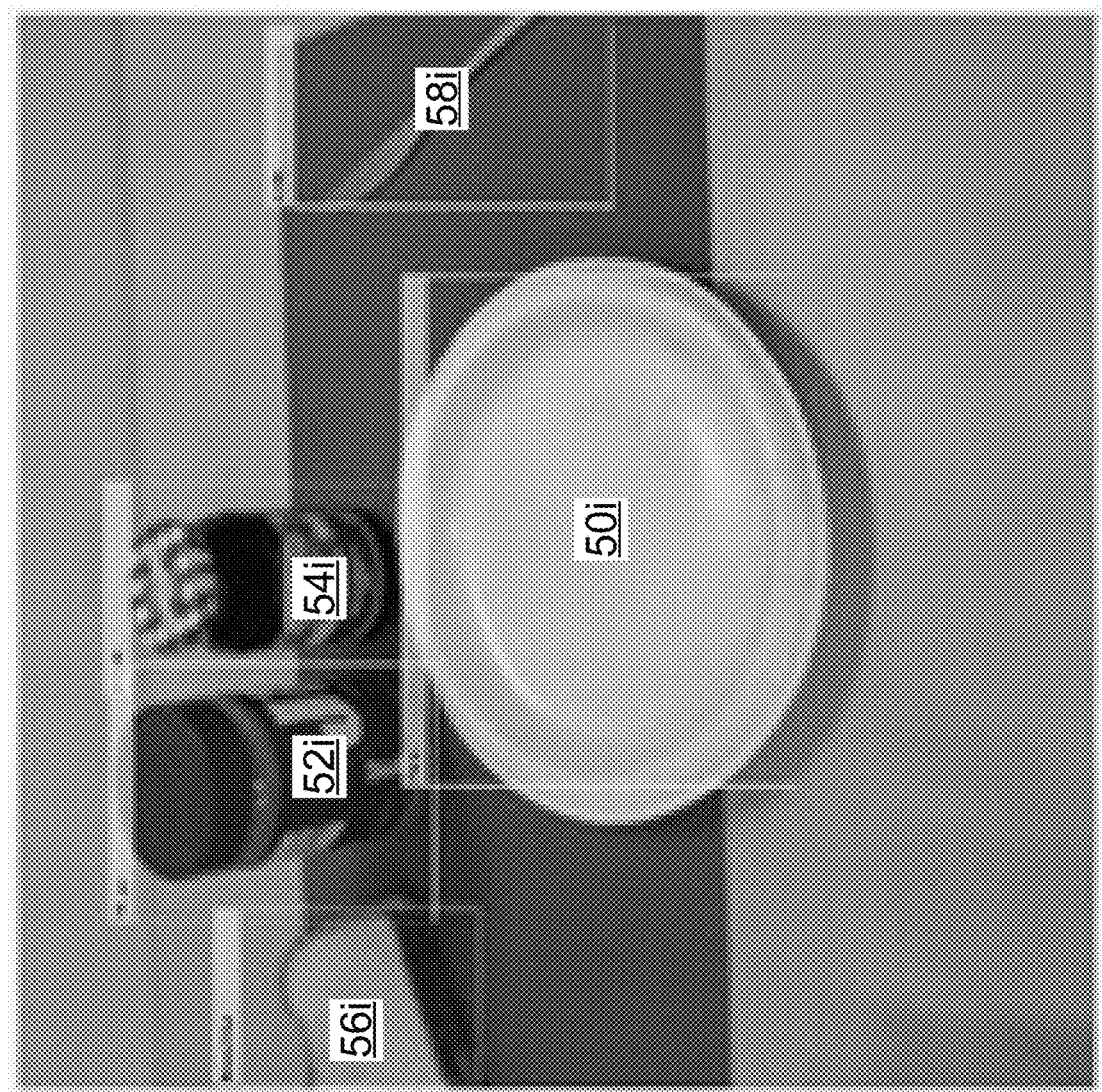
Figure 9B:
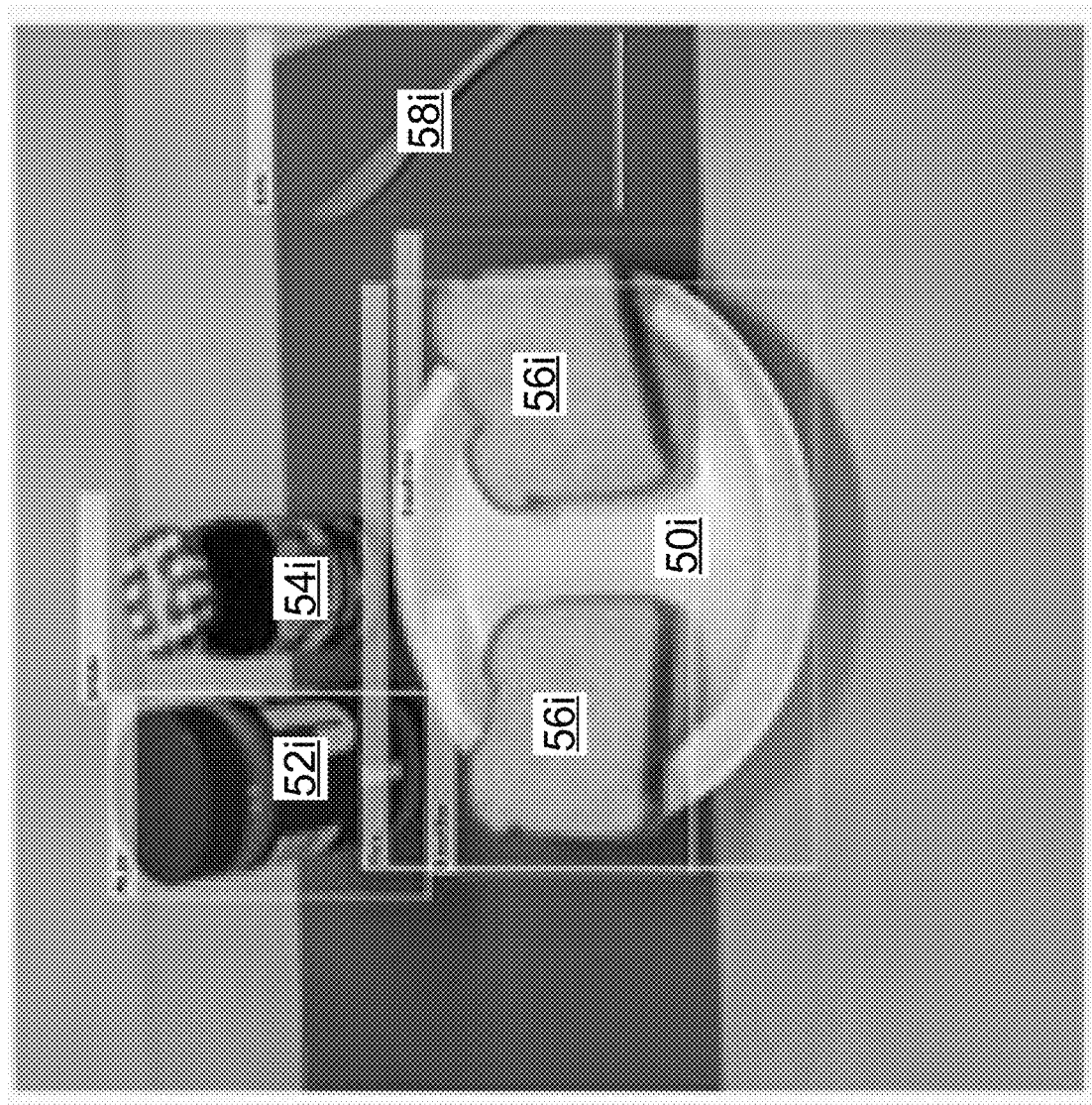

The next step includes presenting the prompt shown in FIG. 8A, which asks the patient to "Place two bread slices on the plate" and provides a graphical representation of the two bread slices 56 on the plate 50. The image frame shown at FIG. 8B corresponding to the time when the prompt of FIG. 8A is first presented shows a state similar to that obtained at the frame of FIG. 7B. FIG. 9B shows the image frame acquired after the patient correctly placed the bread slices 56i on the plate 50i. The object overlap detection function 32 detects overlap of the bread slice objects 56i and the plate 50i. As this is the correct overlap of objects, the triggered activity response is a congratulatory prompt shown in FIG. 9A including the graphical representation of the two slices of bread 56 on the plate 50 along with the text "Nice work!", and the triggered activity response also includes going to the next step of the PB & J sandwich making activity script.

Figure 10B:
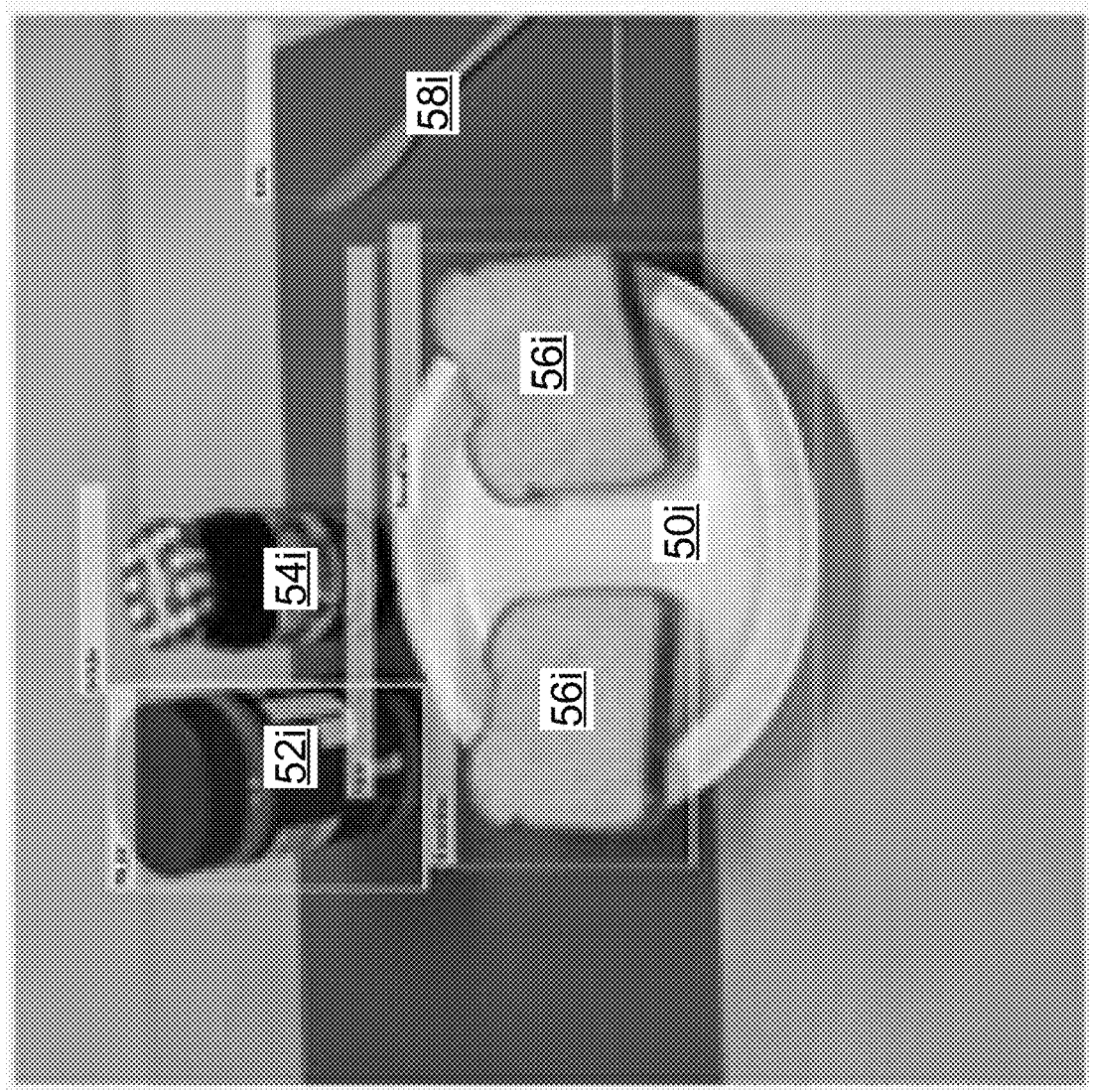
Figure 11A:
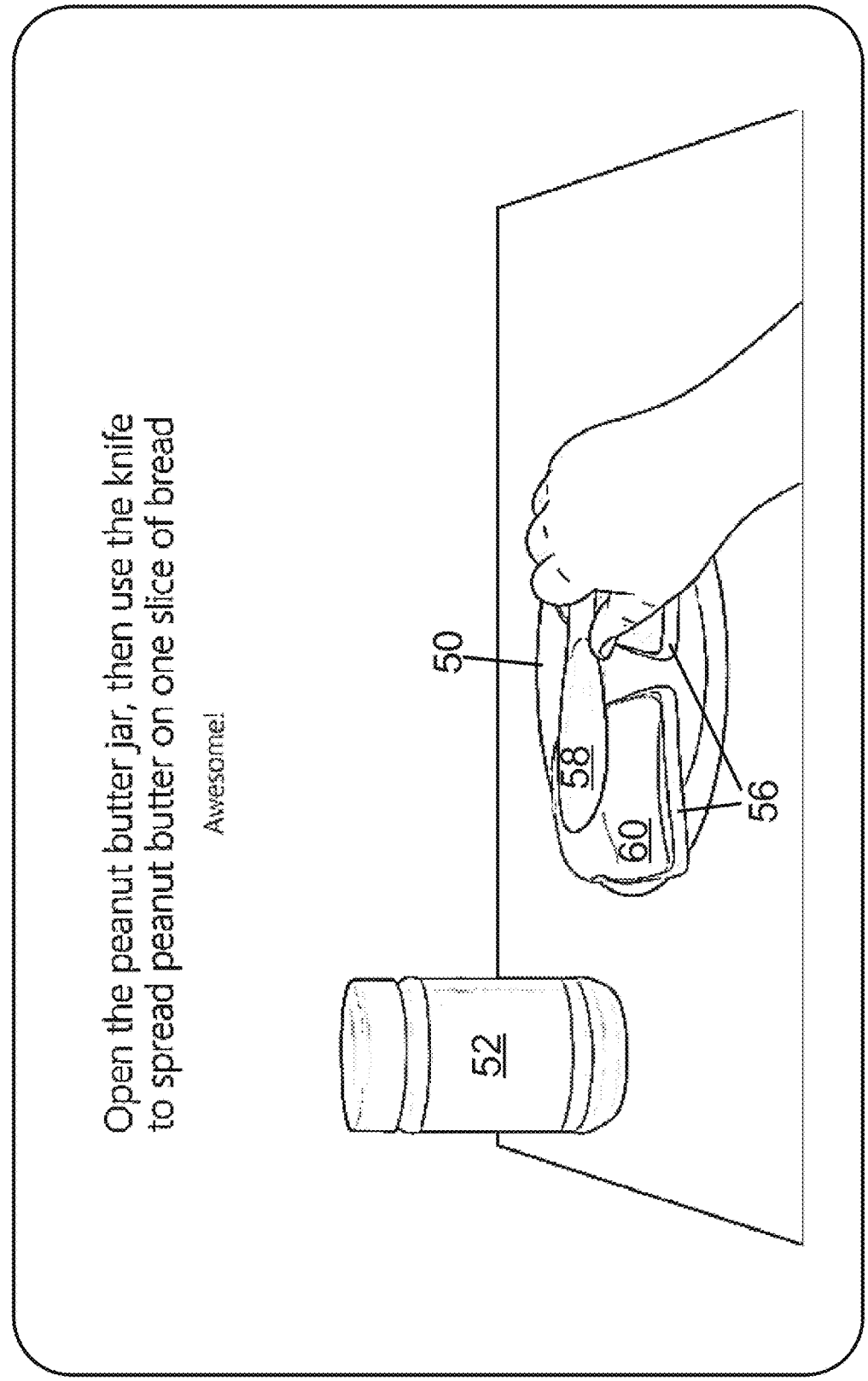
Figure 11B:
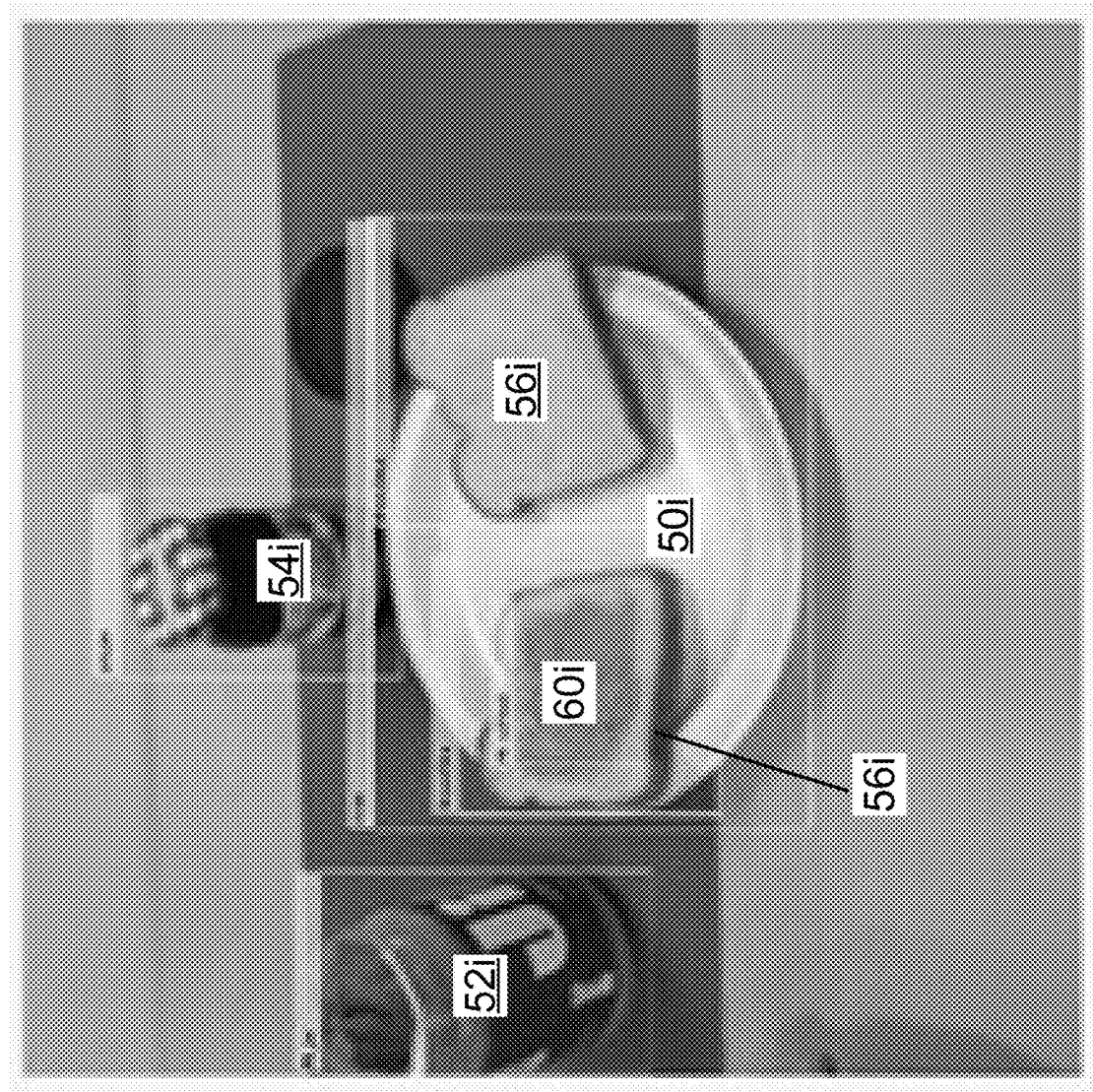

The next step includes presenting the prompt shown in FIG. 10A, which asks the patient to "Open the peanut butter jar, then use the knife to spread peanut butter on one slice of bread" and presents a graphical representation of same. FIG. 10B shows an image frame corresponding to the time the prompt of FIG. 10A is first presented, and the state is similar to that shown by the frame of FIG. 9B. FIG. 11B shows a video frame acquired after the patient successfully performed this operation. The object overlap detection function 32 detects this success as overlap of the peanut butter spread 60i and one slice of bread 56i. (On the other hand, if the patient had incorrectly spread the peanut butter on the plate, not shown, then the object overlap detection function 32 would detect this as an overlap of the peanut butter spread and the plate). The detection of the overlap of the peanut butter spread 60i and the bread slice 56i triggers an action response including the prompt shown in FIG. 11A which includes the congratulatory text "Awesome!" and the same graphical representation as shown in FIG. 10A, and also includes moving to the next step of the activity script.

Figure 12A:
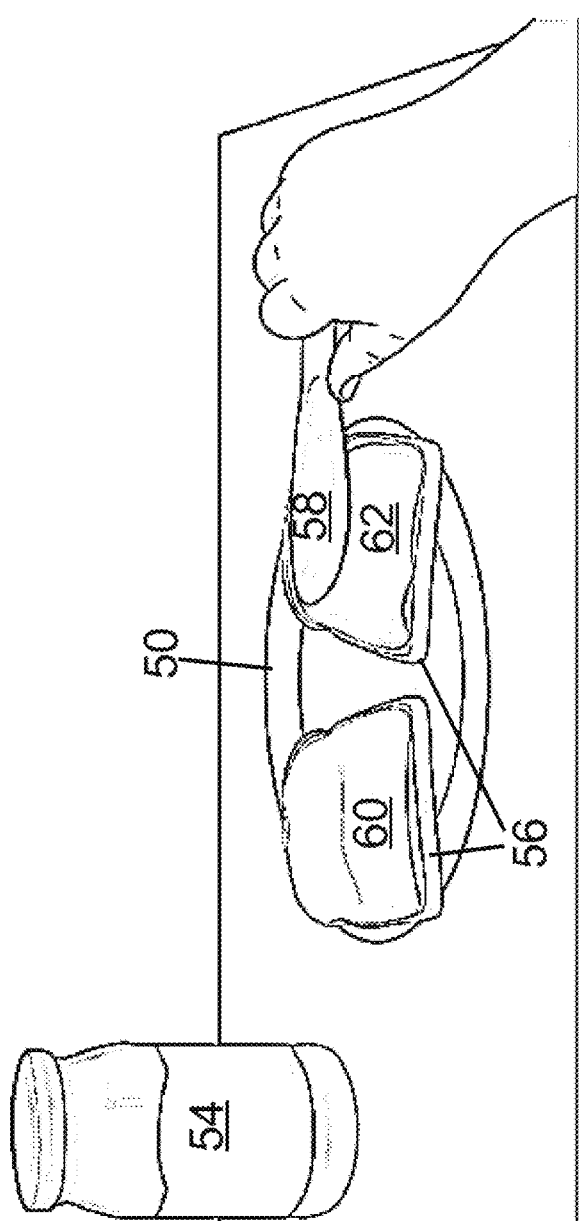
Figure 12B:
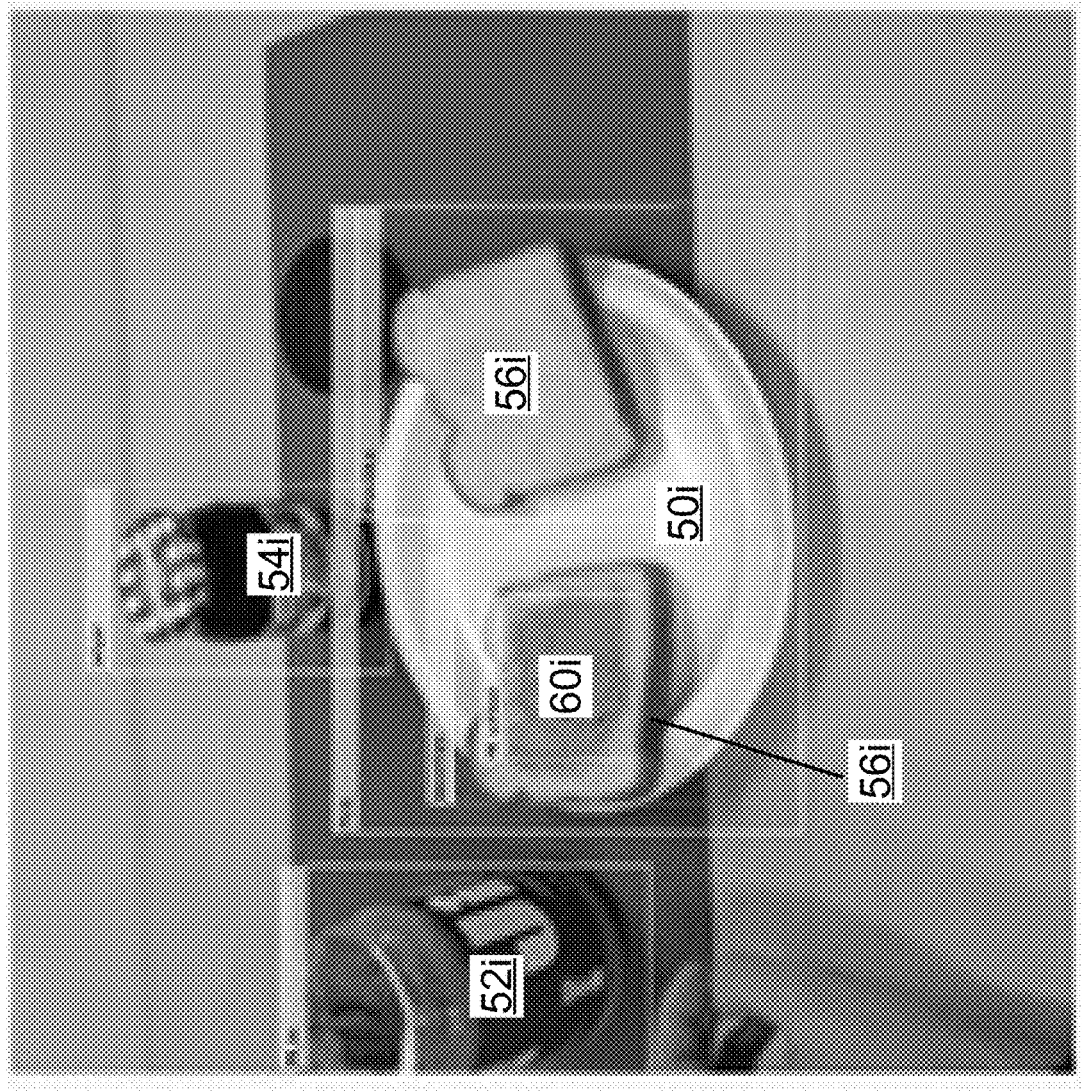
Figure 13A:
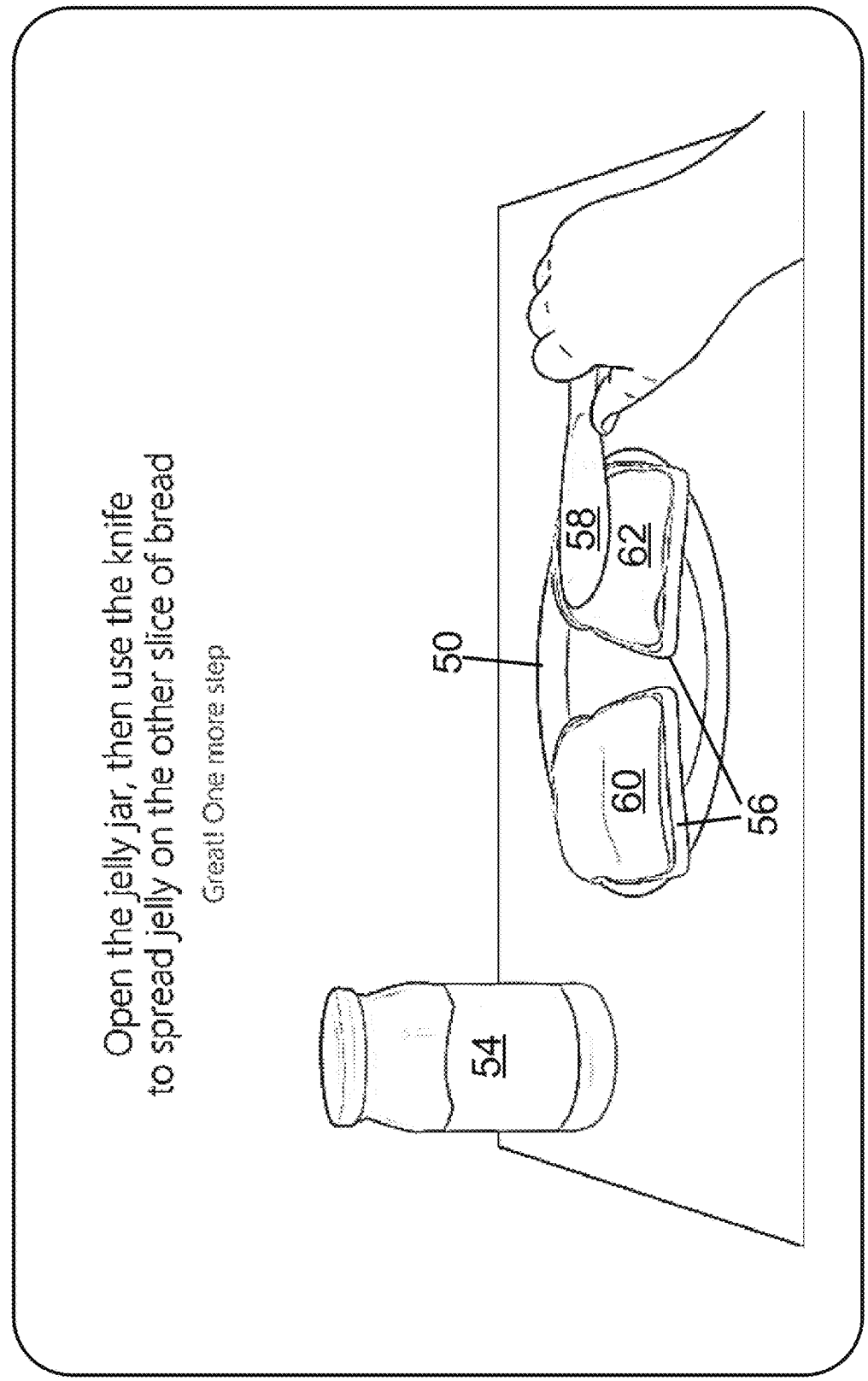
Figure 13B:
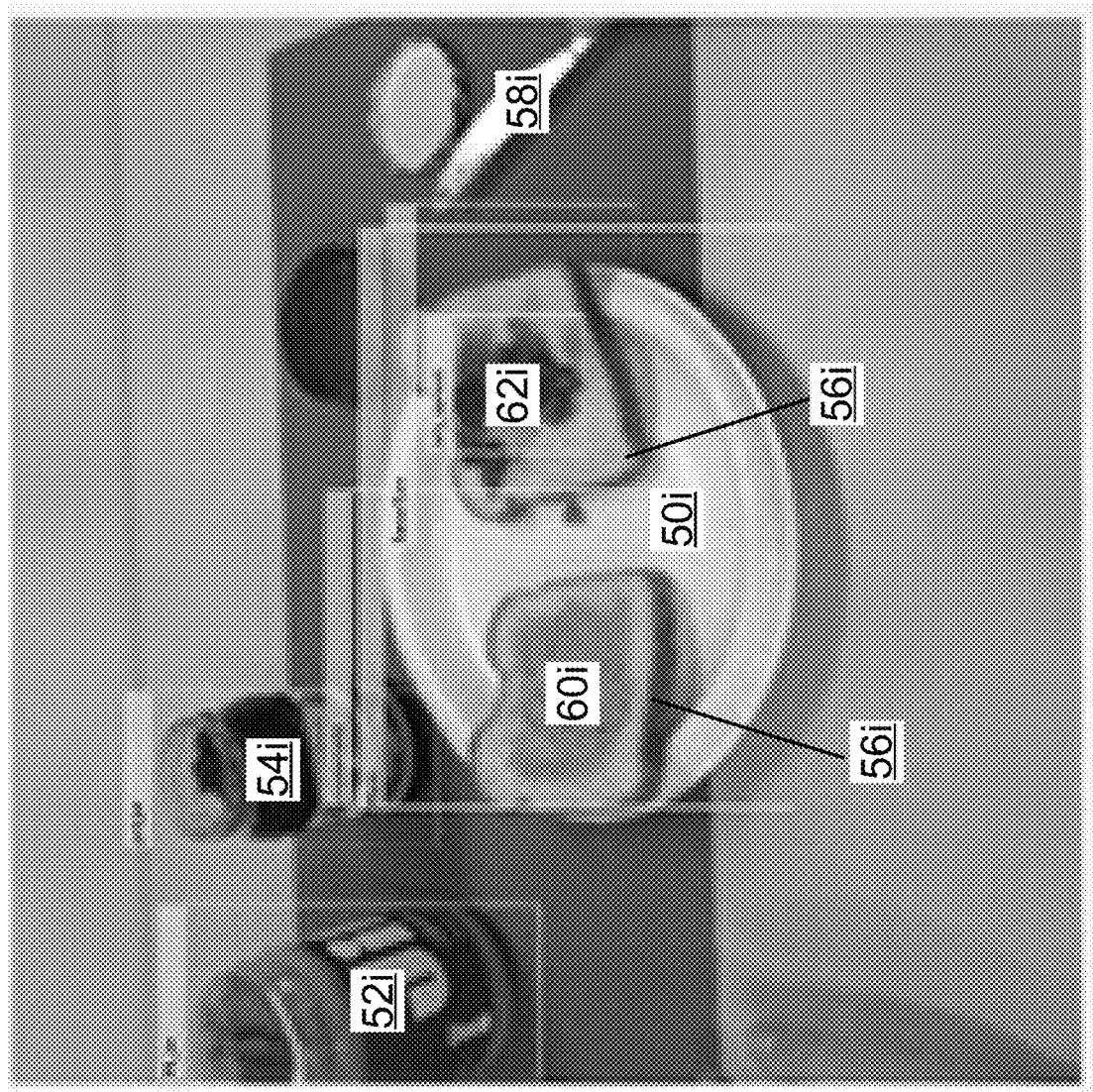

The next step includes presenting the prompt shown in FIG. 12A, which asks the patient to "Open the jelly jar, then use the knife to spread jelly on the other slice of bread" and presents a corresponding graphical representation. FIG. 12B shows an image frame corresponding to the time the prompt of FIG. 12A is first presented, and the state is similar to that shown by the frame of FIG. 11B. FIG. 13B shows a video frame acquired after the patient successfully performed this operation. The object overlap detection function 32 detects this success as overlap of the jelly spread 62i and the other slice of bread 56i. (On the other hand, if the patient had incorrectly spread the jelly on the same slice of bread on which the peanut butter spread is already present, not shown, then the object overlap detection function 32 would detect this as an overlap of the peanut butter spread and the jelly spread). The detection of the overlap of the jelly spread 62i and the other bread slice 56i triggers an action response including the prompt shown in FIG. 13A which includes the congratulatory text "Great! One more step" and the same graphical representation as shown in FIG. 12A, and also includes moving to the next step of the activity script.

Figure 14A:
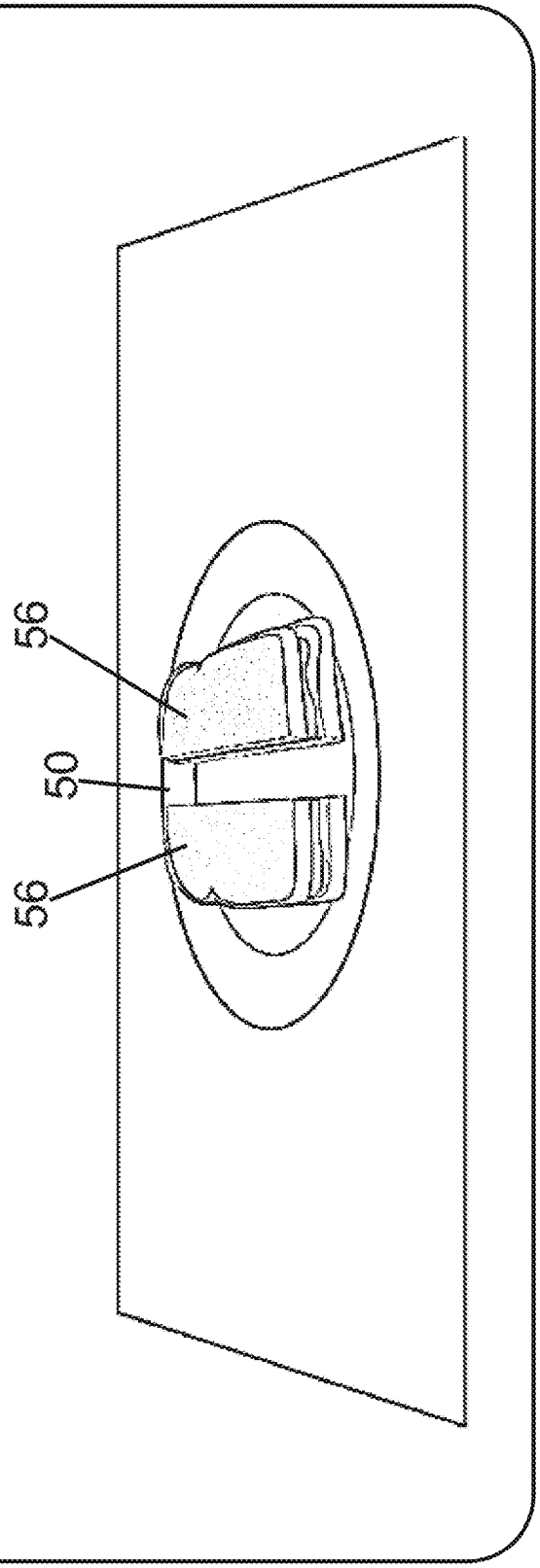
Figure 14B:
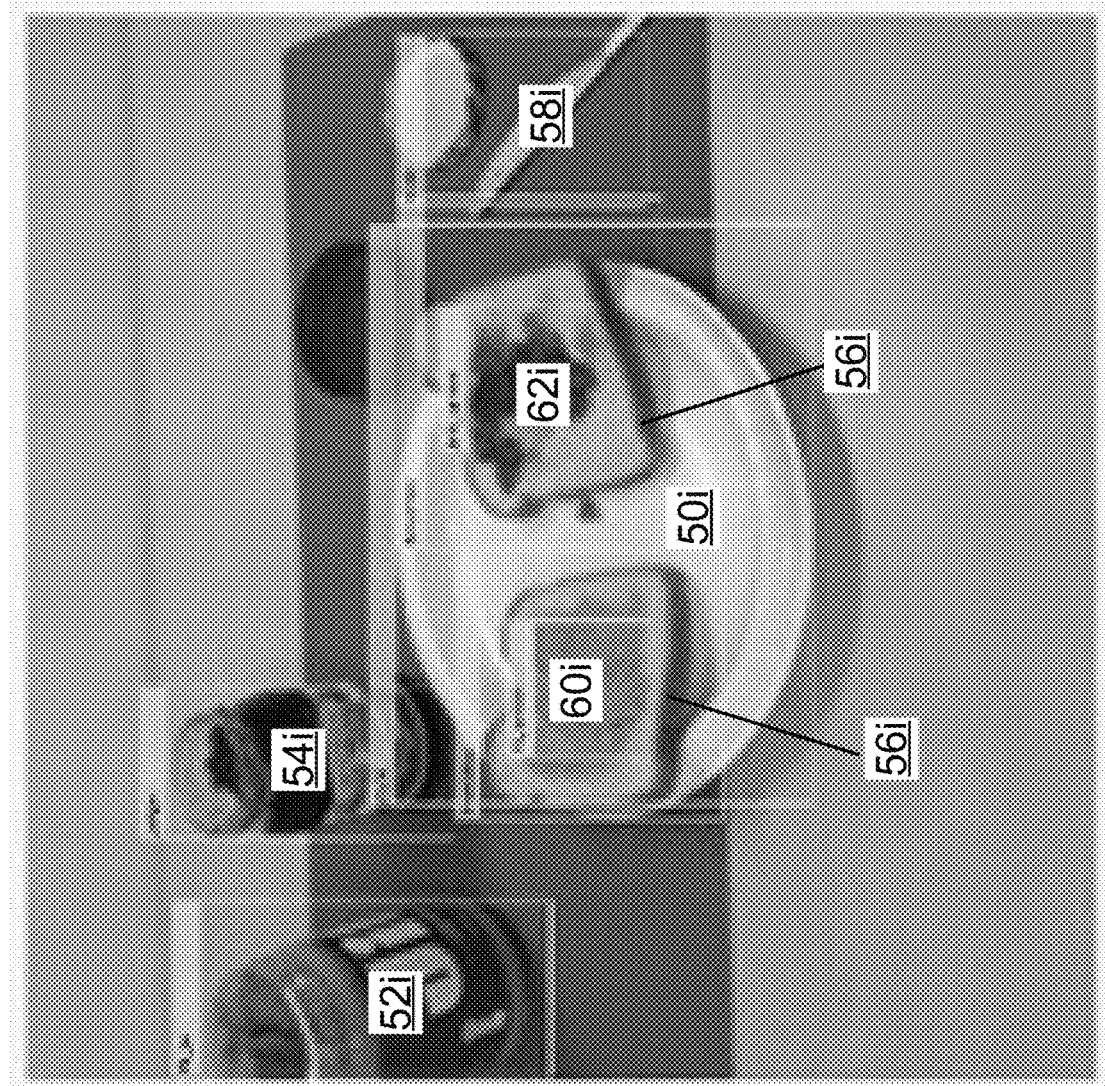

The next step includes presenting the prompt shown in FIG. 14A, which asks the patient to "Press the bread together with the peanut butter and jelly inside, then cut the sandwich in half with the knife" and presents a corresponding graphical representation. FIG. 14B shows an image frame corresponding to the time the prompt of FIG. 14A is first presented, and the state is similar to that shown by the frame of FIG. 13B. FIG. 15B shows a video frame acquired after the patient successfully performed this operation. In one approach, the object order detection function 34 detects this success as two bread slice halves 56iH next to each other. (Other approaches could be used. For example, new objects corresponding to half-sandwiches could be recognized at the object recognition stage.) The detection triggers an action response including the prompt shown in FIG. 15A which includes the congratulatory text "Awesome job! Enjoy your sandwich" at which point the PB & J sandwich making activity script ends.

It will be appreciated that the described execution of the illustrative PB & J sandwich making activity script is merely an example, and that numerous other ADLs can be choreographed by an analogous activity script with suitably tailored prompts and on_event→action detection/triggered response options. For example, in the case of a toothbrushing ADL, the person uses the toothpaste object to dispense a toothpaste spread object onto a toothbrush object, corresponding to the operations of the PB & J activity script choreographed as described with reference to FIGS. 10A-13A and 10B-13B. This type of operation can be generalized to presenting a prompt via the output device asking a person to dispense a substance onto a specified object, and applying the object overlap detection function 32 to detect the substance overlapping an object. Detection by the object overlap function 32 that the substance overlaps an object other than the specified object triggers presenting a prompt indicating the substance has been applied to an incorrect object and asking that the substance be applied to the specified object; whereas, detection by the object overlap function that the substance overlaps the specified object triggers presenting a prompt congratulating the person on dispensing the substance onto the specified object. The prompt in such cases suitably includes displaying an image or graphical representation of the substance dispensed onto the specified object on the display (e.g. as shown in the prompts of FIGS. 10A and 12A).

Similarly, in a generalized case an activity script may include presenting a prompt via the output device asking a person to cause an interaction of a first object and a second object, and applying the object overlap detection function 32 to detect whether the first object and the second object overlap. Detection by the object overlap function that the first object and the second object overlap triggers presenting a prompt congratulating the person on causing the interaction of the first object and the second object; whereas, detection of one of the first or second objects overlapping some other object may be taken as a trigger to prompt the person to correct the error. The prompt may suitably include displaying an image or graphical representation of the interaction of the first object and the second object.

Figure 15A:
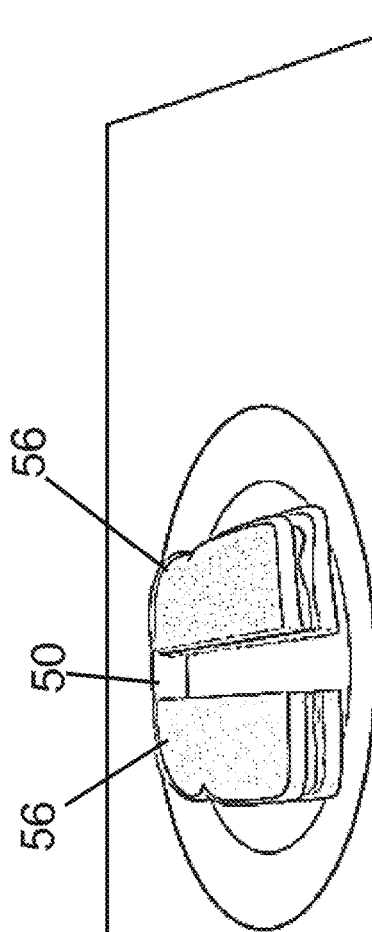
Figure 15B:
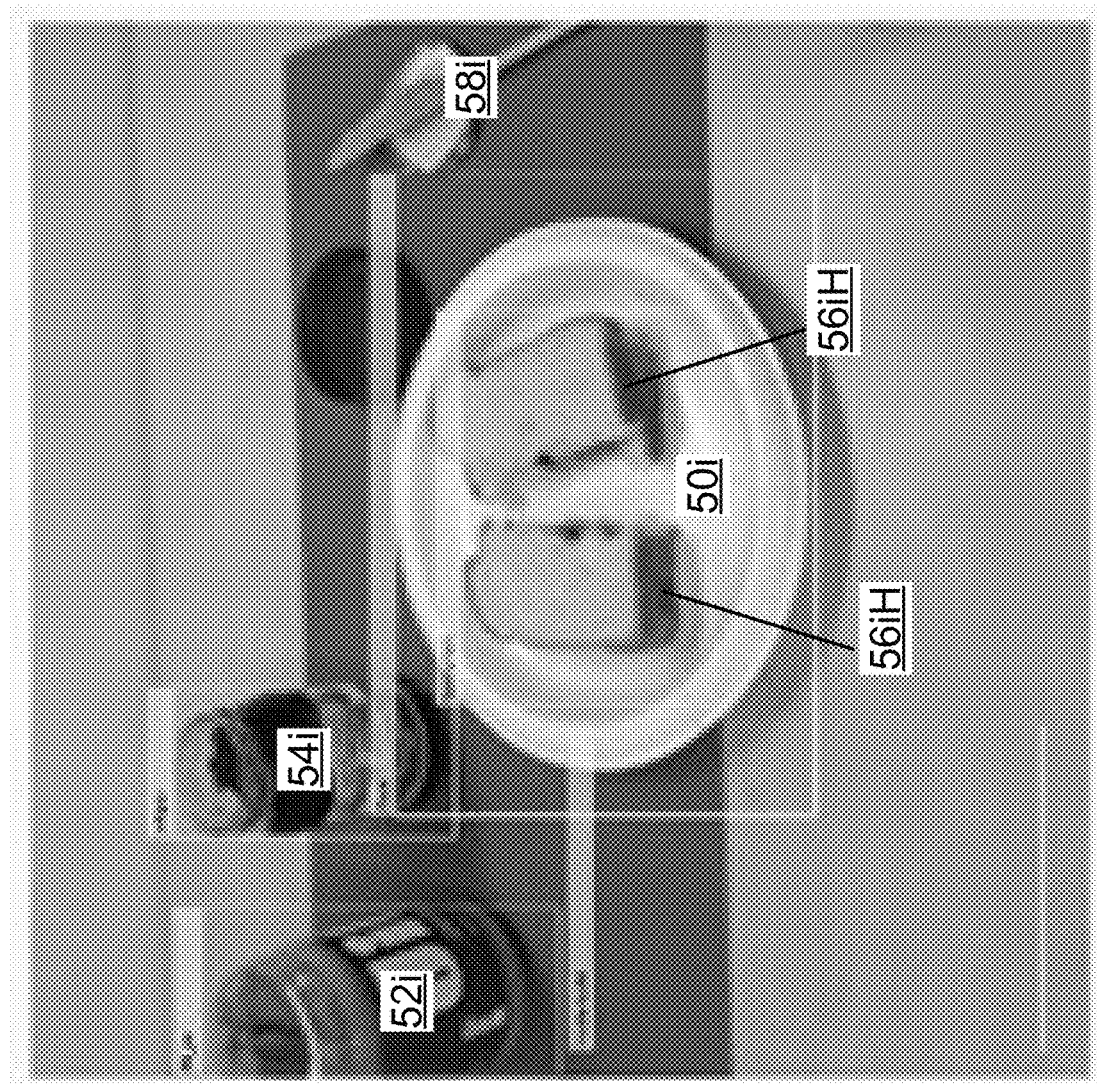
Figure 16:
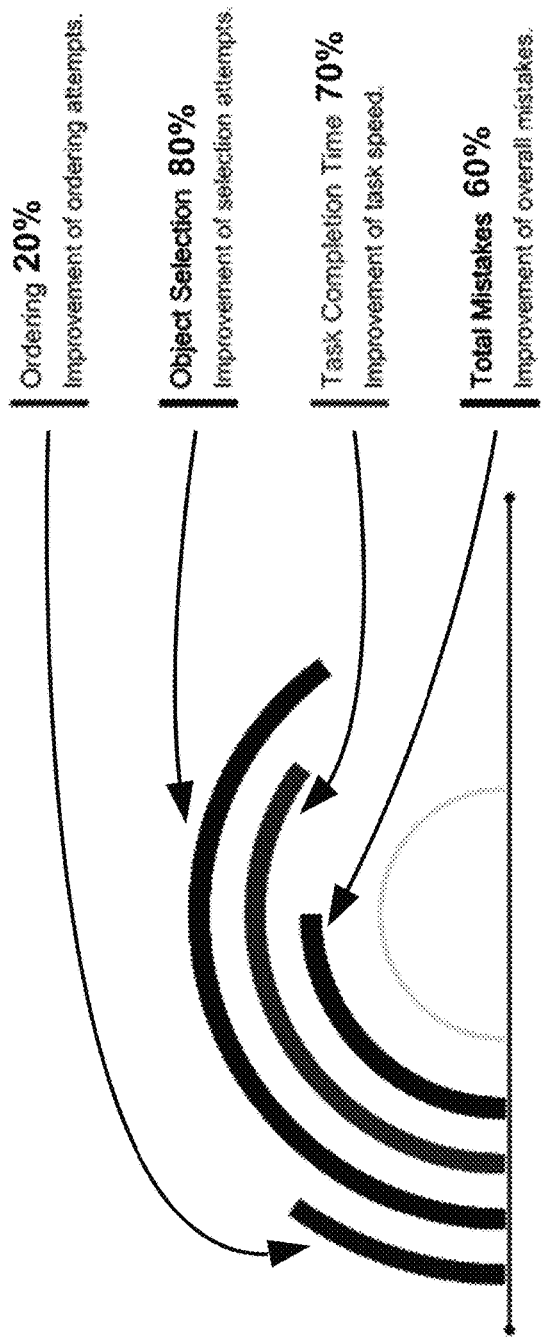
FIG. 16 diagrammatically shows an illustrative display presenting a performance evaluation for the activity of making a PB&J sandwich described with reference to FIGS. 2A-15A and 2B-15B.

With reference to FIG. 16, after completion of the activity script (i.e., after the final congratulatory prompt as shown in FIG. 15A in the illustrative example), the performance evaluation 42 preferably provides a performance report. To this end, the electronic processor is further programmed to track detected events indicating mistakes by the person in performing the activity (e.g., events detected in the image frames of FIGS. 3B and 6B in the illustrative example), and upon completion of the execution of the activity script, a performance report is presented including metrics of the person's performance of the activity determined from the tracked events. Optionally, the electronic processor may be further programmed to quantify times required for the person to perform aspects of the activity based on time intervals between execution of successive steps of the sequence of steps choreographing the activity, and the presented performance report then further includes metrics of the person's performance of the activity determined from the quantified times. FIG. 16 shows an example of a possible performance report.

The disclosed activity assistance systems and methods operate in the real world, using actual objects of the patient (or more generally, the person) to perform the actual ADL, rehabilitation therapy activity, or other activity (as opposed to using a VR system), preferably in the person's own residence (as opposed to at a hospital or other central medical facility). As such, it will be appreciated that the disclosed activity assistance systems can be used in therapeutic or rehabilitation mode, that is, providing a person with practice in performing a scripted ADL or rehabilitation activity. Additionally or alternatively, the disclosed activity assistance systems can be used in assistive mode, that is, providing a person with assistance in performing a scripted ADL as part of the person's daily living.

In addition to assisting in rehabilitation of TBI or other brain diseases, for example the illustrative case of assisting with the peanut butter and jelly sandwich making task as described with reference to FIGS. 2A and 2B through FIG. 16, the disclosed activity assistance system and corresponding methods can also be used in diagnosing or assessing severity of TBI or other brain diseases. This allows for objectively diagnosing (e.g.) TBI severity based on cognitive function. The quantitative diagnosis is suitably based on functional performance of relevant tasks, and can be used in mobile settings such as assessing possible TBI in an injured soldier in a combat situation. This is expected to improve confidence in combat medicine decisions in early intervention of mild to moderate TBI, and improve consistency in medical care. This portable platform for TBI diagnosis suitably uses object detection and interactive scripts to guide individuals through functional activities using physical objects and quantifies performance for accurate diagnosis.

An estimated 5.3 million Americans currently live with a TBI-related disability. Combat-related exposures, as well as routine operational and training activities, put military service members at increased risk of sustaining a TBI with an average of 20,000 U.S. military service members reporting a TBI each year. Despite the high incidence of TBI in military settings, there is no universally accepted battery of assessments to holistically characterize TBI severity. The Glasgow Coma Scale (GCS) is a commonly used screening tool to determine severity of TBI in the acute phase of injury, however, it lacks the sensitivity and specificity to identify clinically relevant cognitive impairment that may impact safety and function in a demanding military setting. Furthermore, while the GCS measures basic physiological response (e.g., withdrawal from noxious stimuli), it fails to quantify functional cognitive deficits associated with TBI, which is an important metric for determining a soldier's ability to safely return to active duty. It is well-established that functional deficits during complex activities and work tasks are underdiagnosed and undertreated in individuals with TBI, yet there is presently no widely accepted assessment of functional cognition post-TBI. Hence, there is an unfulfilled need to develop diagnostic tools that characterize the functional deficits associated with TBI, particularly for military personnel preparing to return to active duty.

Diagnosing TBI severity and readiness to return to active duty is an inherently complex task. It is further complicated in military settings such as battalion aid stations, where time and resources are limited. A basic physical examination of motor function, coordination, reflexes, or so forth is easily conducted in such a forward military setting, but this does not accurately or consistently diagnose mild to moderate TBI. Further, use of currently available TBI assessment tools such as basic neurological exams (e.g., electroencephalogram) or diagnostic imaging (e.g.: computed tomography or magnetic resonance imaging scans) require dedicated equipment, which is prohibitive in forward military settings in which rapid decisions must be made with limited resources.

Ideally, in addition to a physical examination, a battery of neuropsychological tests are administered to assess executive functions (e.g., memory, attention) of individuals with TBI. While valuable for identifying isolated cognitive impairments, neuropsychological tests often fail to capture functional performance deficits, such as those required to do highly complex work tasks. This is due to the qualitative nature of scoring criteria, variability in the assessors themselves, and the limited time assessors are able to devote to each patient due to environment or medical staff availability. Additionally, commonly used impairment-based assessments evaluate single-component cognitive processes in non-distracting and non-stressful environments, they fail to replicate the demands of real-world military environments and tasks. This has led to mild to moderate cognitive impairments, such as slower reaction times and increased task errors, on complex dual tasks (e.g., loading ammunition into a magazine while listening for radio commands) sometimes going undiagnosed. These deficits may lead to decreased safety, inability to complete missions, or increased incidence of injury. In order to objectively measure a soldier's performance in a way that is ecologically valid, an assessment should simulate the vocational demands of military tasks, demonstrate complexity adequate to account for fluid conditions in an operational environment, and challenge known TBI-related vulnerabilities. The disclosed activity assistance system advantageously can be used to diagnose and assess severity of mild to moderate TBI and provides a portable, efficient, and function-focused assessment to improve consistency in characterizing and diagnosing TBI severity of military personnel, resulting in metric-based data measures for return to active duty decision making.

Using the object detection 22 to detect specific objects, the activity assistance system of FIG. 1 identifies and tracks real world objects being manipulated around a work surface or room and assesses human-object interactions. This provides a portable system by using objects readily deployed in the operational environment without the need to add more footprint, and enables administration of an ecologically valid assessment tool that simulates the complex vocational demands of military tasks in an operational environment. The activity assistance system is suitably programmed (e.g., by suitable activity scripts stored in the activity scripts library 44) with task-oriented activities (e.g., military task-oriented activities such as loading a magazine of a firearm with bullets, disassembling and reassembling a firearm, or so forth) allowing individuals with mild to severe TBI to be autonomously assessed on functional activity that directly apply to their lifestyle and/or occupation. Performance-based assessments where subjects complete complex tasks using real-world functional objects is expected to be sensitive to subtle cognitive impairment, such as may be present with mild to moderate TBI. Example functional activities include loading a firearm magazine, assembling a weapon, organizing pills and medications, making a sandwich (e.g., per FIGS. 2A and 2B through 16), and/or so forth. Use of real-world objects available across most military settings will not only improve the ecological validity of the TBI diagnosis or assessment performed using the activity assistance system, but will also improve ease of use and implementation with little additional equipment required for administration.

Figure 17:
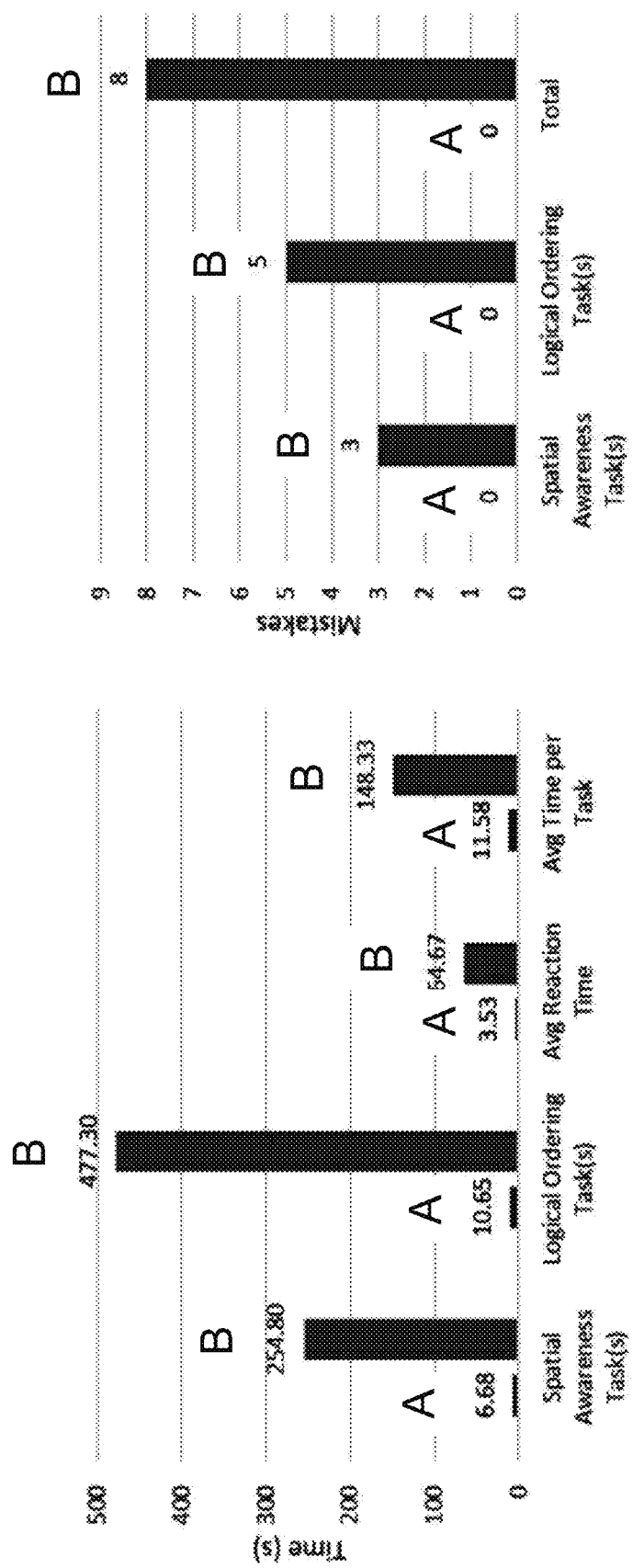
FIG. 17 plots an activity performance comparison between healthy subject and severe TBI subject.

With reference to FIG. 17, evaluation data obtained during a proof-of-concept evaluation with a healthy subject versus a subject with severe TBI are presented. In this evaluation, evaluation data were collected on a patient with severe TBI and a healthy participant performing the same activity with the activity assistance system. For a given activity the activity assistance system prompts the user to perform the steps necessary to complete the exercise. As the user attempts the prompted activity, the system acquires, processes, and interprets frame-by-frame images from the video stream as described with reference to FIG. 1 (or alternatively, the variant system of FIG. 18 to be described) to locate and identify all relevant objects in space. Detected objects include the user's hands, and an activity script 44 was tailored to detect specific military devices, weapons, and other objects commonly used in duty. The system tracks the location of these objects. The goal is for the system to evaluate the user's interactions with the objects in real-time and tracking the number of user errors, speed, sequencing ability, coordination, and other meaningful metrics. While the activity assistance system is able to calculate these various metrics, the data collected in this proof-of-concept evaluation was not perfect, and some manual adjustments were made. These metrics are correlated to currently accepted assessment scales, used to assess cognitive impairment in TBI at higher roles of care settings, and provide a quantitative and highly detailed assessment of the patient's cognitive function. Detailed assessment data of the patient cognitive function is critical for detecting subtle cognitive deficits and gaining a better understanding of an individual's injury and the associated effects. The results of the assessment are statistically analyzed and compiled in a performance report that informs TBI diagnosis.

The activity assistance system provides real-time visual and auditory feedback to the participant based on their performance. Task difficulty and depth of feedback are configurable and vary depending on the individual's injury and ability. Tasks may also be made more challenging by including auditory or visual distractors, or by requiring the individual to multi-task in a complex environment (e.g., load a weapon while simultaneously listening for and responding to commands on a radio). In one approach, activity scripts 44 are provided for three activities with varying degrees of difficulty, to enable assessments to be made in various forward military settings and across a broad spectrum of mild to moderate TBI diagnoses.

FIG. 17 shows performance metrics that factor in elements across steps to evaluate cognitive capabilities including spatial coordination, logical ordering, and reaction time. The reaction time for an action was calculated as the time between when the user was prompted to engage an object and the time when the user engaged with the object. (Again, while the activity assistance system is able to calculate the reaction time, the data collected in this initial proof-of-concept evaluation was not perfect and some manual adjustments were made). There were clear differences in performance between an individual with a severe TBI and a healthy participant, and the activity assistance system was able to capture these differences with high accuracy and precision. Further, when compared against current assessment standards including the modified functional independence measure, the data acquired by the activity assistance system confirmed that the subject exhibited both problem-solving deficits and visual neglect. The ability of the activity assistance system to detect cognitive performance subtleties illustrates its ability to supply a detailed, autonomous assessment and supports feasibility of a faster, more consistent diagnoses, regardless of the military domain, geographic location, or the TBI evaluator's background and training.

More generally, the disclosed activity assistance system is expected to find application in various areas of telehealth, especially in forward military settings. This may, for example, allow non-medical personnel to use the activity assistance system to evaluate their peers in austere environments aided by remote medics or clinicians. As the activity assistance device provides metrics that one can easily compare against an adopted baseline, outposts with little more than tactical communications can benefit from this tool by engaging remote medics or clinicians which talk them through the patient's assessment. For those outposts with satellite communications, they can directly involve these medics and clinicians in the entire process. Connecting the activity assistance system of FIG. 1 (or FIG. 18 to be described) to a remote server via satellite would enable remote medics to interpret performance results in real time. Locally stored video recordings and performance metrics can be transmitted to the remote medics or clinicians. This may entail integrating a satellite communication system in the activity assistance system to enable telecommunication with remote medics or military clinicians.

Moreover, it will be appreciated that the activity assistance systems and methods disclosed herein will find application in areas beyond assisting a person in performing an ADL or rehabilitation activity. For example, the disclosed activity assistance systems and methods may be applied in the context of an assembly line task, equipment servicing task, meal preparation task, culinary recipe execution task, child education task, or other task that is amenable to scripting, In some activity assistance tasks, the presentation of a congratulatory prompt when an event detection indicates a step is successfully completed may be omitted. For example, in an assembly line task the system may execute an activity script choreographing the assembly line task, in which execution of each step includes presenting a prompt via the output device and detecting an event or sequence of events subsequent to the presenting of the prompt. Detection of an error then suitably triggers presenting a prompt indicating the error and asking that a correction be made. But, in the assembly line task, it may be undesirable to present a congratulatory prompt when an event detection indicates the step is successfully completed, since the expectation is that the steps will usually be successfully completed. In a variant approach, congratulatory prompts may be presented randomly or pseudorandomly, in order to provide encouragement without becoming annoying.

With reference back to FIG. 1, the object detection performed by the operation 22 employs CNNs that are trained to detect specific objects delineated by bounding boxes. This type of object detection is fast and flexible, as different CNNs can be trained to detect various types of objects. However, this object detection approach has some disadvantages, including that the delineation of the object by the bounding box is imprecise. The CNN-based approach may also have difficulty detecting objects that are partially occluded, as the partially occluded object has a different shape than the objects used for training (although this can be counteracted in some cases by including training examples of partially occluded objects when training the CNN). The imprecision of bounding box delineation of objects also increases the likelihood that the bounding boxes of neighboring objects may overlap, which can make discrimination of (for example) which object is in front versus which object is behind difficult.

Figure 18:
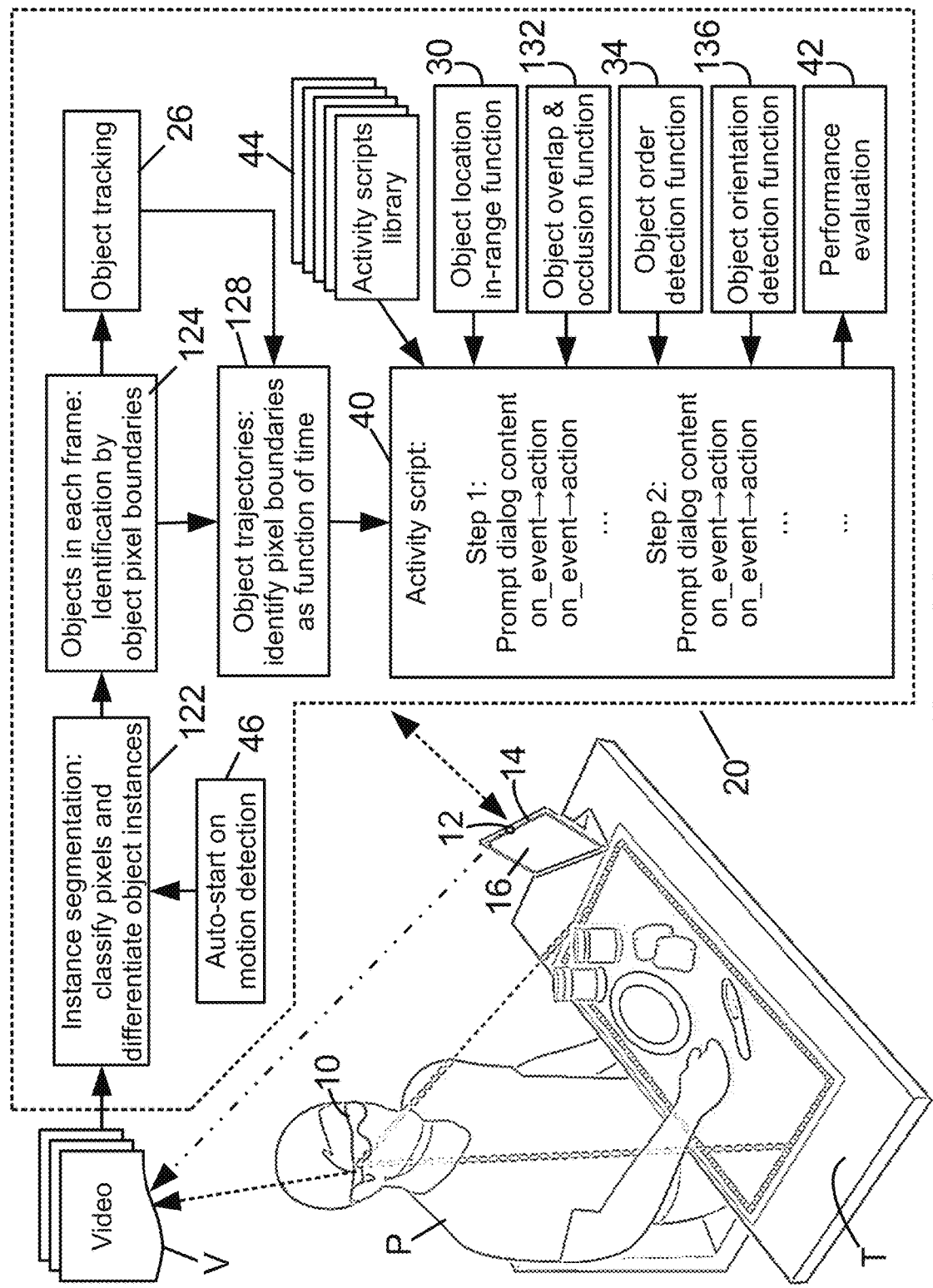
FIG. 18 diagrammatically shows an activity assistance system similar to that of FIG. 1, but in which the object detection delineated by bounding boxes of the embodiment of FIG. 1 is replaced by instance segmentation in the embodiment of FIG. 18.

With reference to FIG. 18, another embodiment of the illustrative activity assistance system of FIG. 1 is shown, which is identical with the activity assistance system of FIG. 1 except that the CNN-based object detection 22 of FIG. 1 is replaced in the embodiment of FIG. 18 by object detection using instance segmentation 122; and accordingly block 24 of FIG. 1 in which objects in each frame are identified by bounding boxes is replaced in the embodiment of FIG. 18 by a block 124 of FIG. 18 in which objects in each frame are identified by object pixel boundaries, and block 28 of FIG. 1 in which object trajectories are identified as (positions of) bounding boxes as a function of time is replaced in the embodiment of FIG. 18 by a block 128 of FIG. 18 in which object trajectories are identified as (positions of) pixel boundaries of the objects as a function of time.

The object detection using instance segmentation 122 employs an approach in which pixels are classified by object type and object instances are differentiated. Instance segmentation can provide object orientation and high-detail resolution by detecting exact pixel-boundaries of objects. There are a range of instance segmentation techniques known in the image processing arts (e.g., pixel classification followed by blob connectivity analysis; or instance segmentation using mask regional CNNs trained for specific object types (see He et al., "Mask R-CNN", arXiv:1703.06870v3 [cs.CV] 24 Jan. 2018), and the instance segmentation 122 of FIG. 18 can employ any such technique. Other object identification techniques known in the image processing arts including blob detection and template matching can be used to identify standardized objects. These methods may be used in place of, or in combination with, object detection methods using CNNs depending on the types of objects used in a task.

In the following, an example of using the activity assistance system of FIG. 18 is described with reference to the activity of Assessment of Military Multitasking performance (AMMP). The AMMP assessment includes a battery of military-specific, functional tasks that require varying levels of complex cognitive processing. In the example here presented, an AMMP task calls for a soldier to load bullets into a firearm magazine. (More generally, the AMMP task may include a weapon disassembly/assembly task or other military-related AMMP task). In such a task, the bullets may be scattered on a table in various orientations. Furthermore, as the soldier inserts a bullet into the magazine, the bullet may be occluded by the soldier's fingers or (as it enters the magazine) by the magazine itself (or conversely the bullet may occlude the magazine). Object detection using bounding boxes can have difficulty handling these complex object orientations and potential occlusions.

A particular advantage of employing instance segmentation to perform the object detection on video frames is that it provides information on the object orientation and can also provide information for extraction occlusion relationships (e.g., does object A occlude object B, i.e. is object A in front of object B?; or, does object B occlude object A, i.e. is object B in front of object A?). For example, in the magazine loading AMMP task, the object detection 22 of FIG. 1 employs object recognition CNNs that delineate objects by bounding boxes. The bounding boxes determined by the object detection therefore delineate the magazine by a bounding box and delineate bullets by respective bullet bounding boxes and the hand by a bounding box. While these bounding boxes provide locational information, they do not provide information on the orientation of the represented objects, nor in the case of overlapping bounding boxes do they provide information on which object is occluding and which is occluded.

On the other hand, in processing of the same image of a magazine loading task using the object detection by instance segmentation 122 of the activity assistance system embodiment of FIG. 18, the instance segmentation 122 identifies the magazine by a pixel boundary and likewise identifies each of the bullets by corresponding bullet pixel boundaries and the hand by a pixel boundary. Unlike the bounding boxes produced by the object detection 22 of FIG. 1, the pixel boundaries produced by the instance segmentation 122 of FIG. 18 identify the exact pixel boundaries of the corresponding objects. These pixel boundaries therefore contain information sufficient to identify the orientations of the respective objects. Moreover, where two objects overlap, the order of overlap (that is, which object is the occluding object and which object is the occluded object) can be identified for objects with standard shapes based on which object has its shape "reduced" by occlusion. Hence, in the activity assistance system of FIG. 18, the object overlap detection function 32 of FIG. 1 can be suitably replaced (or augmented) by an object overlap and occlusion detection function 132 in the system of FIG. 18, which identifies which both the overlap and which object is occluded. Likewise, and object orientation detection function 136 can be provided to detect the orientation of an object with a standard shape based on the exact pixel boundary identified by the object detection by instance segmentation 122 of the activity assistance system embodiment of FIG. 18. Other event detection functions (not shown) can be similarly enabled by identification of the exact pixel boundary of an object, such as identifying the object size (for objects which may vary in size, e.g. quantifying the amount of peanut butter that is spread onto a bread slice in the main illustrative example presented herein).

As already noted, the object detection by instance segmentation 122 of the activity assistance system embodiment of FIG. 18 can facilitate more accurate scripting of activities such as the AMMP magazine loading task. Another possible application thusly enabled is a pill sorting application, in which a person is tasked with sorting pills into a pill organizer. Here the ability to identify the exact pixel boundary of each pill facilitates distinguishing different types of pills, since for example a blood pressure medication pill may have a different shape and/or size compared with another type of pill. (Pill color may also be useful in making such distinctions). The pill sorting task takes advantage of the common pharmaceutical industry practice of employing standard pill sizes, shapes, and colors for different pharmaceutical pills.

Another type of task that an benefit from the precise pixel boundary delineation of objects provided by the object detection by instance segmentation 122 of the activity assistance system embodiment of FIG. 18 is tasks related to diagnosis and/or assessment of visual neglect, which is a neuropsychological condition in which damage to the visual cortex or other brain area relating to vision results in the person having difficulty in recognizing a spatial portion of an observed object. For example, in hemispatial neglect, the damage is to one hemisphere of the brain and typically manifests as reduced or non-existent recognition of one-half of an observed object. In one suitable approach, the person performing the test may be asked to trace the outline of an observed object using a finger, pointing stick, or the like. As the object detection by instance segmentation 122 provides the exact pixel boundary of the object, any systematic difference between this pixel boundary and the outline traced by the person can be identified as potentially due to visual neglect; and, indeed, the spatial portion of the object that the person has difficulty visually perceiving can be similarly identified. The preferred embodiments have been illustrated and described. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. An activity assistance system comprising:
   a video camera arranged to acquire video of a person performing an activity;
   an output device configured to output human-perceptible prompts; and
   an electronic processor programmed to execute an activity script comprising a sequence of steps choreographing the activity wherein the execution of each step includes presenting a prompt via the output device and detecting an event or sequence of events subsequent to the presenting of the prompt;
   wherein each event is detected by performing object detection on the video to detect one or more objects depicted in the video delineated by bounding boxes or by pixel boundaries of the respective one or more objects and applying one or more object-oriented image analysis functions to detect a spatial or temporal arrangement of one or more of the detected objects; and
   each event detection triggers an action comprising at least one of presenting a prompt via the output device and/or going to another step of the activity script.

2. The activity assistance system of claim 1 wherein the activity script choreographs an activity of daily living (ADL) and steps of the activity script include presenting a congratulatory prompt when an event detection indicates the step is successfully completed.

3. The activity assistance system of claim 1 wherein the activity script choreographs a rehabilitation activity and steps of the activity script include presenting a congratulatory prompt when an event detection indicates the step is successfully completed.

4. The activity assistance system of claim 1 wherein the activity script includes a step which includes:
   presenting a prompt via the output device asking a person to place a set of objects in a correct order; and
   applying an object order detection function to detect whether a spatial order of the set of objects is in the correct order;
   wherein detection by the order detection function that the spatial order of the set of objects is not in the correct order triggers presenting a prompt indicating the incorrect order and asking that the order be corrected.

5. The activity assistance system of claim 4 wherein the output device comprises a display and the prompt asking the person to place the set of objects in a correct order includes displaying an image or graphical representation of the set of objects in the correct order on the display.

6. The activity assistance system of claim 1 wherein the activity script includes a step which includes:
   presenting a prompt via the output device asking a person to place a specified object in a specified location; and
   applying an object location in-range function to detect an object in the specified location;
   wherein detection by the object in-range function that an object other than the specified object is in the specified location triggers presenting a prompt indicating the incorrect object has been placed in the specified location and asking that the specified object be placed in the specified location.

7. The activity assistance system of claim 6 wherein the output device comprises a display and the prompt asking the person to place the specified object in the specified location includes displaying an image or graphical representation of the specified location with the specified object in the specified location on the display.

8. The activity assistance system of claim 1 wherein the activity script includes a step which includes:
   presenting a prompt via the output device asking a person to dispense a substance onto a specified object; and
   applying an object overlap detection function to detect the substance overlapping an object;
   wherein detection by the object overlap function that the substance overlaps an object other than the specified object triggers presenting a prompt indicating the substance has been applied to an incorrect object and asking that the substance be applied to the specified object.

9. The activity assistance system of claim 8 wherein the output device comprises a display and the prompt asking the person to dispense the substance onto the specified object includes displaying an image or graphical representation of the substance dispensed onto the specified object on the display.

10. The activity assistance system of claim 1 wherein the activity script includes a step which includes:
    presenting a prompt via the output device asking a person to cause an interaction of a first object and a second object; and
    applying an object overlap detection function to detect whether the first object and the second object overlap;
    wherein detection by the object overlap function that the first object and the second object overlap triggers presenting a congratulatory prompt.

11. The activity assistance system of claim 10 wherein the output device comprises a display and the prompt asking the person to dispense the substance onto the specified object includes displaying an image or graphical representation of the interaction of the first object and the second object.

12. The activity assistance system of claim 1 wherein the video camera comprises a video camera of smart glasses or a webcam of a computer.

13. The activity assistance system of claim 1 wherein each event is detected by performing object detection on the video to detect one or more objects depicted in the video delineated by bounding boxes.

14. The activity assistance system of claim 1 wherein each event is detected by performing object detection comprising instance segmentation on the video to detect one or more objects depicted in the video delineated by pixel boundaries of the respective one or more objects.

15. The activity assistance system of claim 1 wherein the output device includes at least one of a display of a computer, a display of smart glasses, a loudspeaker of the computer, and/or a loudspeaker of the smart glasses.

16. An activity assistance system comprising:
    a video camera arranged to acquire video of a person performing an activity;
    an output device configured to output human-perceptible prompts; and
    an electronic processor programmed to:
        execute an activity script comprising a sequence of steps choreographing the activity wherein the execution of each step includes presenting a prompt via the output device and detecting an event or sequence of events subsequent to the presenting of the prompt;
        track detected events indicating mistakes by the person in performing the activity; and upon completion of the execution of the activity script, presenting a performance report including metrics of the performance of the activity determined from the tracked events;

wherein each event is detected by performing object detection on the video to detect one or more objects depicted in the video and applying one or more object-oriented image analysis functions to detect a spatial or temporal arrangement of one or more of the detected objects; and each event detection triggers an action comprising at least one of presenting a prompt via the output device and and/or going to another step of the activity script.

17. The activity assistance system of claim 16 wherein the electronic processor is further programmed to generate a quantitative traumatic brain injury (TBI) diagnosis based on the metrics of the performance of the activity determined from the tracked events.

18. The activity assistance system of claim 16 wherein the electronic processor is further programmed to:
calculate a reaction time for an event as a time between presenting a prompt to engage an object via the output device and a time of detection of an event comprising the person engaging with the object.

19. The activity assistance system of claim 16 wherein the electronic processor is further programmed to:
quantify times required for performing aspects of the activity based on time intervals between execution of successive steps of the sequence of steps choreographing the activity;
wherein the presented performance report further includes metrics of the performance of the activity determined from the quantified times.

20. An activity assistance system comprising:
a video camera arranged to acquire video of a person performing an activity;
an output device configured to output human-perceptible prompts; and
an electronic processor programmed to execute an activity script comprising a sequence of steps choreographing the activity wherein the execution of each step includes presenting a prompt via the output device and detecting an event or sequence of events subsequent to the presenting of the prompt;
wherein each event is detected by performing object detection on the video to detect one or more objects depicted in the video and applying one or more object-oriented image analysis functions to detect a spatial or temporal arrangement of one or more of the detected objects; and
each event detection triggers an action comprising at least one of presenting a prompt via the output device and and/or going to another step of the activity script
wherein the electronic processor comprises a laptop or notebook computer and the video camera comprises a webcam of the laptop or notebook computer having its field of view (FOV) angled downward to image a surface on which the laptop or notebook computer is disposed when a display of the laptop or notebook computer is oriented to be viewed by the person performing the activity.

21. An activity assistance method comprising:
using a video camera, acquiring video of a person performing an activity;
using an electronic processor, executing an activity script comprising a sequence of steps choreographing the activity wherein the execution of each step includes presenting a prompt via an output device and detecting an event or sequence of events subsequent to the presenting of the prompt, wherein each event is detected by performing object detection on the video to detect one or more objects depicted in the video and applying one or more object-oriented image analysis functions to detect a spatial or temporal arrangement of one or more of the detected objects; and
responsive to each event detection, performing an action comprising at least one of presenting a prompt via the output device and and/or going to another step of the activity script;
wherein the activity script choreographs an activity of daily living (ADL) or a rehabilitation therapy activity.

22. The activity assistance method of claim 21 wherein the activity script includes a step which includes:
presenting a prompt via the output device asking a person to place a set of objects in a correct order wherein the prompt includes a displayed image or graphical representation of the set of objects in the correct order; and
applying an object order detection function to detect whether a spatial order of the set of objects is in the correct order;
wherein in response to detection by the order detection function that the spatial order of the set of objects is not in the correct order, a prompt is presented indicating the incorrect order and asking that the order be corrected; and
wherein in response to detection by the order detection function that the spatial order of the set of objects is in the correct order, a congratulatory prompt is presented.

23. The activity assistance method of claim 21 wherein the activity script includes a step which includes:
presenting a prompt via the output device asking a person to place a specified object in a specified location wherein the prompt includes a displayed image or graphical representation of the specified location with the specified object in the specified location; and
applying an object location in-range function to detect an object in the specified location;
wherein in response to detection by the object in-range function that an object other than the specified object is in the specified location, a prompt is presented indicating the incorrect object has been placed in the specified location and asking that the specified object be placed in the specified location; and
wherein in response to detection by the object in-range function that the specified object is in the specified location, a congratulatory prompt is presented.

24. The activity assistance method of claim 21 wherein the activity script includes a step which includes:
presenting a prompt via the output device asking a person to dispense a substance onto a specified object wherein the prompt includes a displayed image or graphical representation of the substance dispensed onto the specified object; and
applying an object overlap detection function to detect the substance overlapping an object;
wherein in response to detection by the object overlap function that the substance overlaps an object other than the specified object, a prompt is presented indicating the substance has been applied to an incorrect object and asking that the substance be applied to the specified object; and
wherein in response to detection by the object overlap function that the substance overlaps the specified object, a congratulatory prompt is presented.

25. The activity assistance method of claim 21 wherein the activity script includes a step which includes:
- presenting a prompt via the output device asking a person to cause an interaction of a first object and a second object wherein the prompt includes a displayed image or graphical representation of the interaction of the first object and the second object; and
- applying an object overlap detection function to detect whether the first object and the second object overlap;
- wherein in response to detection by the object overlap function that the first object and the second object overlap, a congratulatory prompt is presented.

26. The activity assistance method of claim 21 further comprising:
- tracking detected events indicating mistakes by the person in performing the activity;
- quantifying times required for the person to perform aspects of the activity based on time intervals between execution of successive steps of the sequence of steps choreographing the activity; and
- upon completion of the execution of the activity script, presenting a performance report including metrics of the performance of the activity determined from the tracked events and metrics of the performance of the activity determined from the quantified times.

* * * * *